(12) United States Patent
Gibbs

(10) Patent No.: US 10,548,685 B2
(45) Date of Patent: Feb. 4, 2020

(54) MEDICAL STAND

(71) Applicant: Trevor S. Gibbs, Naperville, IL (US)

(72) Inventor: Trevor S. Gibbs, Naperville, IL (US)

(73) Assignee: Anestand, Inc., Naperville, IL (US)

( * ) Notice: Subject to any disclaimer, the term of this patent is extended or adjusted under 35 U.S.C. 154(b) by 6 days.

(21) Appl. No.: 15/789,979

(22) Filed: Oct. 21, 2017

(65) Prior Publication Data
US 2018/0110583 A1 Apr. 26, 2018

Related U.S. Application Data

(60) Provisional application No. 62/411,304, filed on Oct. 21, 2016.

(51) Int. Cl.
| | |
|---|---|
| *A61G 13/10* | (2006.01) |
| *A61B 90/50* | (2016.01) |
| *A61B 50/15* | (2016.01) |
| *A61B 50/10* | (2016.01) |
| *A61B 50/33* | (2016.01) |
| *A61B 90/57* | (2016.01) |
| *A47B 23/04* | (2006.01) |

(52) U.S. Cl.
CPC .............. *A61B 90/50* (2016.02); *A61B 50/10* (2016.02); *A61B 50/15* (2016.02); *A61B 50/33* (2016.02); *A47B 23/04* (2013.01); *A61B 2090/571* (2016.02)

(58) Field of Classification Search
CPC ... A61B 50/20; A61B 50/33; A61B 2090/571; A61M 5/1415; A61G 13/101; A47B 23/02
See application file for complete search history.

(56) References Cited

U.S. PATENT DOCUMENTS

| | | | | |
|---|---|---|---|---|
| 3,696,920 A | * | 10/1972 | Lahay | A61B 50/20 128/DIG. 26 |
| 4,018,412 A | * | 4/1977 | Kees, Jr. | A61G 13/101 248/214 |
| 4,445,859 A | * | 5/1984 | Hoffmeister | A61G 15/16 433/77 |
| 4,889,231 A | * | 12/1989 | Foote | B65D 1/34 206/363 |
| D323,560 S | | 1/1992 | Boyce | |
| 5,114,023 A | | 5/1992 | Lavin | |
| 5,435,448 A | * | 7/1995 | Kempen | A61M 5/1417 206/364 |
| 5,586,163 A | * | 12/1996 | Goldstein | A61B 50/33 211/85.13 |
| 5,664,750 A | * | 9/1997 | Cohen | F16M 11/041 248/229.15 |
| 6,182,662 B1 | * | 2/2001 | McGhee | A61M 5/1415 128/845 |

(Continued)

*Primary Examiner* — Bradley Duckworth
(74) *Attorney, Agent, or Firm* — Chicago IP Law; Steven M. Evans

(57) ABSTRACT

A medical stand for use during anesthesia procedures, comprising a tray, a clamp to be connected to a fixed support, wherein upper and lower jaws of the clamp include circular and rectangular slots for grasping and securing the clamp to various types of stationary objects, and wherein jaws of the clamp pass by each other in a fully closed position, and flexible pole having a first end connected to a releasable connector on the bottom of the tray and a second end opposing the first end connected to the clamp.

18 Claims, 23 Drawing Sheets

(56) References Cited

U.S. PATENT DOCUMENTS

| | | | | |
|---|---|---|---|---|
| 6,345,873 B1* | 2/2002 | Kim | ............... | F16L 3/223 |
| | | | | 248/68.1 |
| 6,471,167 B1* | 10/2002 | Myers | ............... | A61G 13/101 |
| | | | | 248/125.9 |
| 6,619,599 B2* | 9/2003 | Elliott | ............... | A61M 5/1415 |
| | | | | 248/125.8 |
| 6,629,615 B2* | 10/2003 | Kim | ............... | F16L 3/223 |
| | | | | 211/85.13 |
| 6,644,636 B1* | 11/2003 | Ryan | ............... | B25B 5/06 |
| | | | | 269/156 |
| 7,395,563 B2* | 7/2008 | Whitmore, III | ...... | A61B 6/0442 |
| | | | | 248/276.1 |
| 7,527,600 B2* | 5/2009 | Farmer | ............... | A47B 57/565 |
| | | | | 362/257 |
| 7,731,138 B2* | 6/2010 | Wiesner | ............... | A61M 5/1415 |
| | | | | 248/160 |
| D626,239 S * | 10/2010 | Lia | ............... | D24/185 |
| 8,621,692 B1* | 1/2014 | Kring | ............... | A61G 13/101 |
| | | | | 248/228.3 |
| 9,033,162 B2 | 5/2015 | Brotzman | | |
| 9,463,070 B2 | 10/2016 | Kerns | | |
| D816,848 S * | 5/2018 | Cole | ............... | D24/184 |
| 2002/0104934 A1 | 8/2002 | Elliott | | |
| 2005/0045785 A1* | 3/2005 | Cohen | ............... | E04F 11/1812 |
| | | | | 248/214 |
| 2005/0267449 A1* | 12/2005 | Edoga | ............... | A61B 50/20 |
| | | | | 606/1 |
| 2006/0278785 A1 | 12/2006 | Wiesner | | |
| 2008/0308698 A1* | 12/2008 | Steppe | ............... | A61L 2/26 |
| | | | | 248/274.1 |

\* cited by examiner

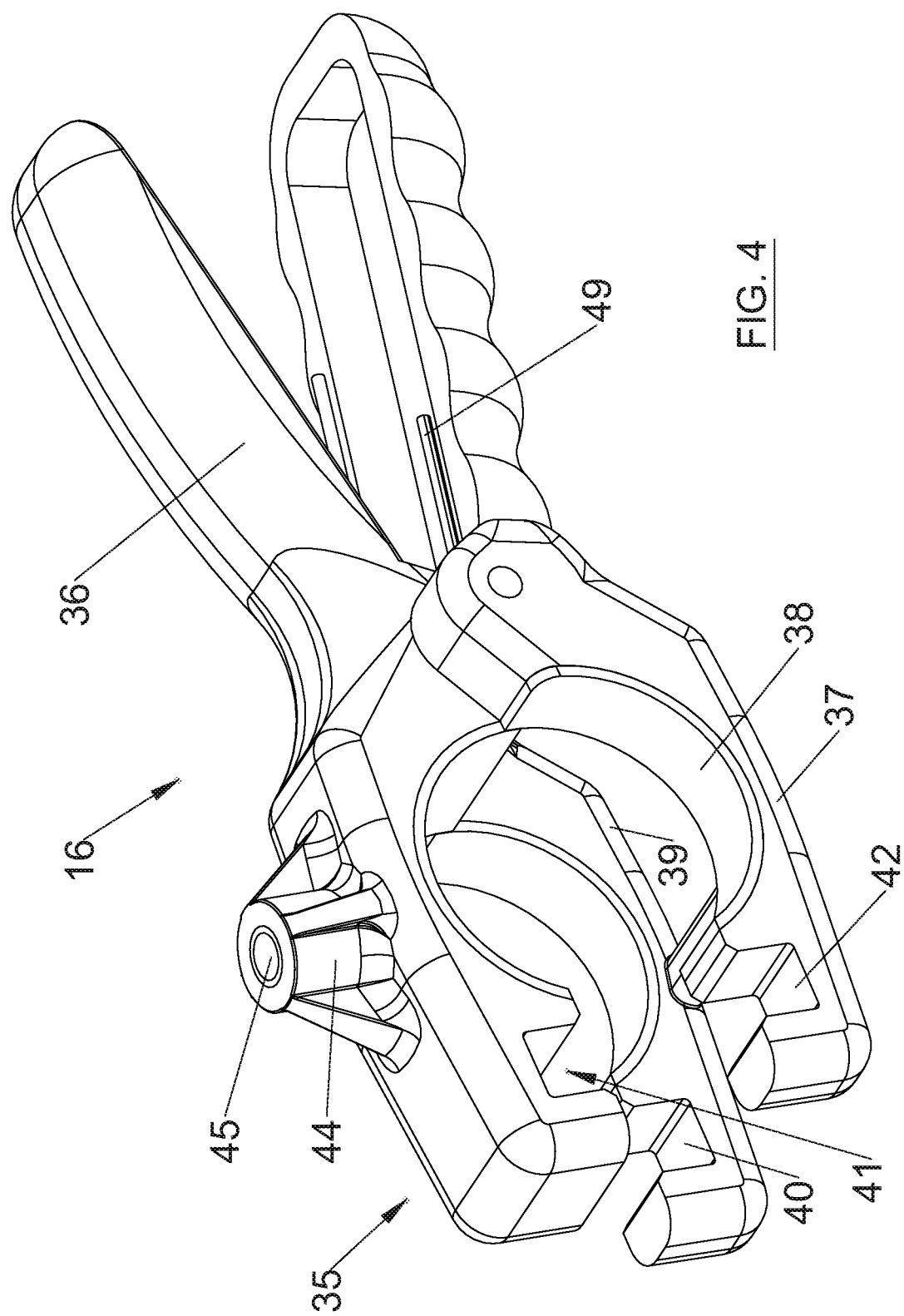

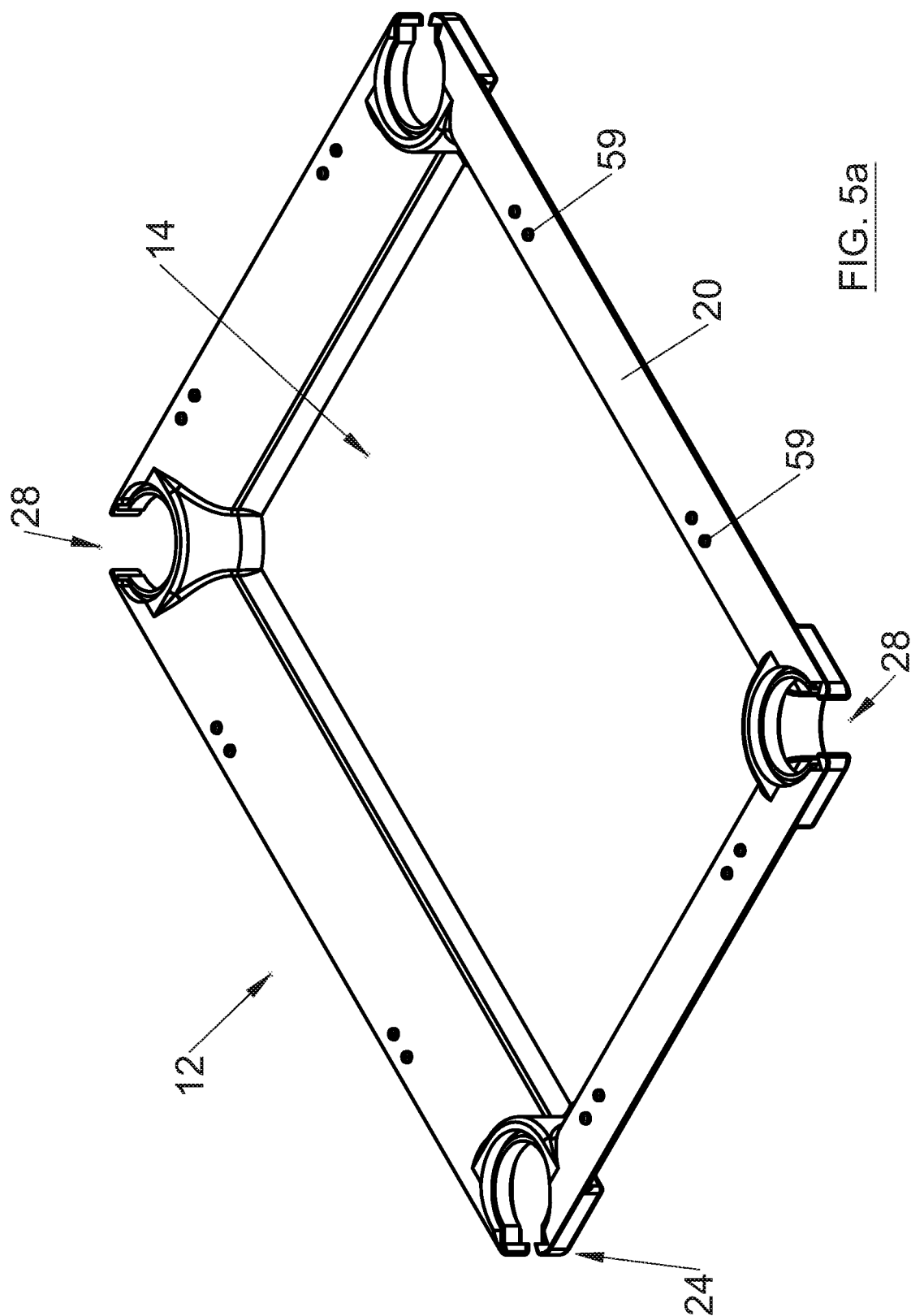

MEDICAL STAND

CROSS-REFERENCE TO RELATED APPLICATIONS

This non-provisional patent application claims priority and benefit of provisional patent application entitled "Medical Stand" filed on Oct. 21, 2016, having Ser. No. 62/411,304, which is incorporated by reference.

BACKGROUND OF THE INVENTION

Field of the Invention

The present invention relates generally to equipment used in anesthesia procedures, and more particularly, to a medical stand for supporting anesthesia equipment.

Description of Related Art

Anesthesia is necessary to allow patients to tolerate procedures, surgeries, and studies that otherwise would be impossible. Anesthesia can come in a variety of forms including general anesthesia, sedation or regional anesthesia (in the form of numbing a part of the body). Anesthesia providers (anesthesiologists, nurse anesthetists and anesthesia assistants) utilize a myriad of equipment to anesthetize patients in a variety of medical locations. To keep patients safe during anesthesia, both invasive and non-invasive monitors are required. Special invasive lines and monitors allow for the administration of medications, fluids and blood. Other noninvasive monitors (blood pressure cuff, pulse oximeter, and electrocardiography (ECG) leads) contribute to a patients' safety as well. From induction (putting the patient off to sleep) through emergence (waking the patient up), it is essential to have the supplies in a convenient and hygienic location.

General anesthesia is an anesthetic wherein the patient is completely unaware and unresponsive to noxious stimulus. This type of anesthesia is used for the most common surgeries (such as appendectomy, knee arthroscopy, gallbladder removal, etc). For induction of general anesthesia, the patient needs an intravenous catheter (IV) as a vehicle to administer fluids and medications, medications to put the patient to sleep, a breathing tube to assist the patient breathing, suction tubing and a suction probe (to suction any secretions or emesis in the mouth), and a laryngoscope. Additional supplies that need accounted for by the anesthesia provider include: anesthesia circuit (the corrugated tubing that attaches the breathing tube to the ventilator), the anesthesia mask (that covers the patient's mouth and nose as they fall off to sleep), the cords that connect the patient to the monitor and the IV injection port. Once the patient is on the table and monitors have been applied, the masks placed over the mouth and nose to give the patient supplemental oxygen. This mask is attached to the anesthesia breathing circuit (described previously). Several medications are then given through the IV port that cause the patient to fall asleep. The oral pharynx is then visualized with a laryngoscope, suctioned with a suction probe to remove any secretions before they fall into the lungs and then a breathing tube (endotracheal tube) is placed into the trachea. The breathing tube is then connected to the anesthesia circuit and the tube is secured in place with tape. It is essential to tape this in place as removal of the tube before the patient is ready could be a fatal event. It is also essential to tether the breathing circuit to protect that from pulling on the breathing tube.

Currently many of these supplies are set on the patient's chest and fall on the floor at key times during induction. Other times key supplies are set on carts behind the anesthesia provider which is inconvenient and due to the fact they are not as immediately available, less safe. It has long been both an inconvenience for anesthesia providers not having a place to set their equipment. While this lack of organization and space is an inconvenience to anesthesia providers, more importantly, it is a risk for the patient as often the IV tubing and the port fall on the floor as do the syringes, suction probe and breathing tube. Often times these medications are set right on the patient prior to their use. This is a risk to the patients in multiple ways. First it's an infection risk. A dirty piece of equipment poses a risk to all patients and even more risk should these patients be immunocompromised (which many patients fall into this class). The second major risk is that a key piece of equipment might fall out of reach at just the moment they are needed. Examples of this include: suction probe falling to the ground right when a patient vomits, the breathing tube falling right at the time it is about to be placed, syringes being unavailable when the medications needs to be given promptly (such as when the patient has laryngospasm, dangerously low blood pressure, cardiac arrhythmia, etc). It would be a major benefit to the patient and the anesthesia provider to keep all supplies at arms length for immediate availability in a hygienic manner.

Hospital acquired infections have become a hot issue recently. Anesthesiologists give an average of 20 injections through the IV per case. The IV port has been viewed as also a port for infection to enter the body. During the surgery the IV port is often found resting on the floor due the length of the IV tubing and currently the lack of a place to secure it. While the IV should be cleaned before each injection, often the cleaning process is omitted. This is either due to the urgency of the situation and needing to give medications quickly and the risk of infection is lower than the risk of delaying the medications or just the inconvenience of cleaning the port for so many injections. While neither reason justifies risking an infection, the reality is that often times these dirty ports are introducing pathogens to the patient. Laryngoscopes, endotracheal tubes and syringes are set in locations that are not designed for the job.

As previously mentioned there are other types of anesthesia besides general anesthesia. Spinal, Epidural, peripheral nerve block and sedation are all frequently employed by anesthesia providers around the world. Each of these types of anesthesia require their own supplies that share the same lack of space described for general anesthesia to hygienically hold supplies.

Anesthesia can be performed in a variety of locations. These locations include, but are not limited to: operating room, MRI scanner, CT scanner, physician and dental offices, neurointerventional labs, and cardiology catheterization lab. These locations are often not designed for anesthesia and lack an apparatus to hold the corrugated tubing that attaches to the breathing tube. These locations outside of the operating room use different tables than those in the operating room. Operating room tables have a side rail that allows surgical devices to bind to during an operation. A device to hold specialized anesthesia equipment would need to bind to something other than the bed side rail. A device that can bind to a plurality of fixed surfaces would be of benefit. Specifically, a device that binds to an operating room table rail, IV poles, gurneys, intensive care unit (ICU) beds, and hospital beds is currently unavailable, but would be a major help to anesthesia providers and patients.

Placement of invasive monitors and lines in the patient's arms is a challenge as there is no dedicated location to set anesthesiologist equipment and it is difficult for anesthesiologist to hold their needed equipment. A patient's arms are directly out at their side on a very narrow arm board. One common monitor is the placement of a radial artery catheter to measure blood pressure every second of the surgery rather than to measure the blood pressure every few minutes when the blood pressure cuff reads the pressure. To place a catheter in the artery of the wrist it requires sterile gloves, a needle, catheter, sterile wash, tubing connecting the catheter and monitor and adhesive dressing. These supplies are often set on the ground, balanced on the patient's arm (which then fall) or set on a sitting stool. These locations are at best poorly designed for the job (and often fail to hold the supplies and they fall), and at worst, dirty and a route for infection. An apparatus that could hold our special supplies would be of help.

Some types of surgeries in specific situations would benefit from an even more specialized tray to hold supplies. For instance, cardiac surgery has lots of IV lines. A tray that would hold medications and lots of lines would be very helpful. Additionally, the ability to have a device that can change the type of attached tray would be of major benefit. Accordingly, there is a need for a medical stand that supports various equipment used in surgical and anesthesia procedures.

ASPECTS AND SUMMARY OF THE PRESENT INVENTION

One aspect of the present invention is to provide a medical stand for keeping anesthesia and surgical equipment sterile and off the floor.

A further aspect of the present invention is to organize anesthesia and surgical equipment, thus making the equipment more easily accessible to medical professionals.

Another aspect of the present invention is to provide a location for securely and safely mounting medical equipment during medical procedures.

An additional aspect of the present invention is to provide a device that can securely and safely mount anesthesia and surgical equipment to various surfaces and locations, such as an operating bed rail and an IV pole.

A further aspect of the present invention is to provide a device for holding anesthesia equipment that can be quickly and easily moved and secured to various fixtures and objects in various locations.

In order to provide these aspects and others, the present invention provides a a medical stand tray that holds essential anesthesia supplies. The tray binds IV tubing, corrugated tubing of the anesthesia breathing circuit, suction tubing, and has raised sides to prevent the contents of the tray from rolling off the planar surface. Third, the corner feature has a novel design that binds the cords and tubes used by anesthesia providers. Fourth, the hooks on the support post keeps the floor free of cords that inhibit the movement of IV poles and could trip the anesthesia provider or prevent the movement of the OR table when it is required to be moved. Fifth, the ability to detach and attach a specific tray unique to anesthesia needs is novel. Sixth, the flexible post allows the tray to be moved in a position that is most useful. It also allows the tray to be leveled when the Operating room table is positioned in various positions.

The present invention also allows for the attachment of a device to hold biologic hazards like hypodermic needles. It also allows for the attachment of a holster for the suction probe. The medical stand of the present invention is extremely versatile, adaptable, and portable. It can adapt by attaching different trays to meet specific needs. The medical stand is very portable due to the fact that it can be taken anywhere anesthesia is needed, and it can bind to pretty much anything, such as a hospital bed, gurney rail, etc. The medical stand lends a hand where other tables and stands can't due to space constraints.

The clamp enables anesthesiologists to quickly grab either the operating bed side rail or another fixed support, such as the IV pole. A double lower jaw enables the upper jaw of the clamp to "pass through" and between the lower jaws, thus enabling the clamp to grasp very small diameter poles.

The foregoing has outlined, rather broadly, the preferred features of the present invention so that those skilled in the art may better understand the detailed description of the invention that follows. Additional features of the invention will be described hereinafter that form the subject of the claims of the invention. Those skilled in the art should appreciate that they can readily use the disclosed invention and specific embodiments as a basis for designing or modifying other structures for carrying out the same purposes of the present invention, and that such other structures do not depart from the spirit and scope of the invention in its broadest form.

BRIEF DESCRIPTION OF THE DRAWINGS

FIG. 4 is a perspective view of the clamp of the medical stand shown in FIGS. 1a-3b;

FIG. 5a is a is perspective view of the top of the tray of the medical stand shown in FIGS. 1a-3b;

FIG. 5b is a perspective view of the bottom of the tray shown in FIG. 5a;

FIG. 10b is a perspective view of the clamp shown in FIG. 10a;

DETAILED DESCRIPTION OF THE PREFERRED EMBODIMENTS

Figure 1A:
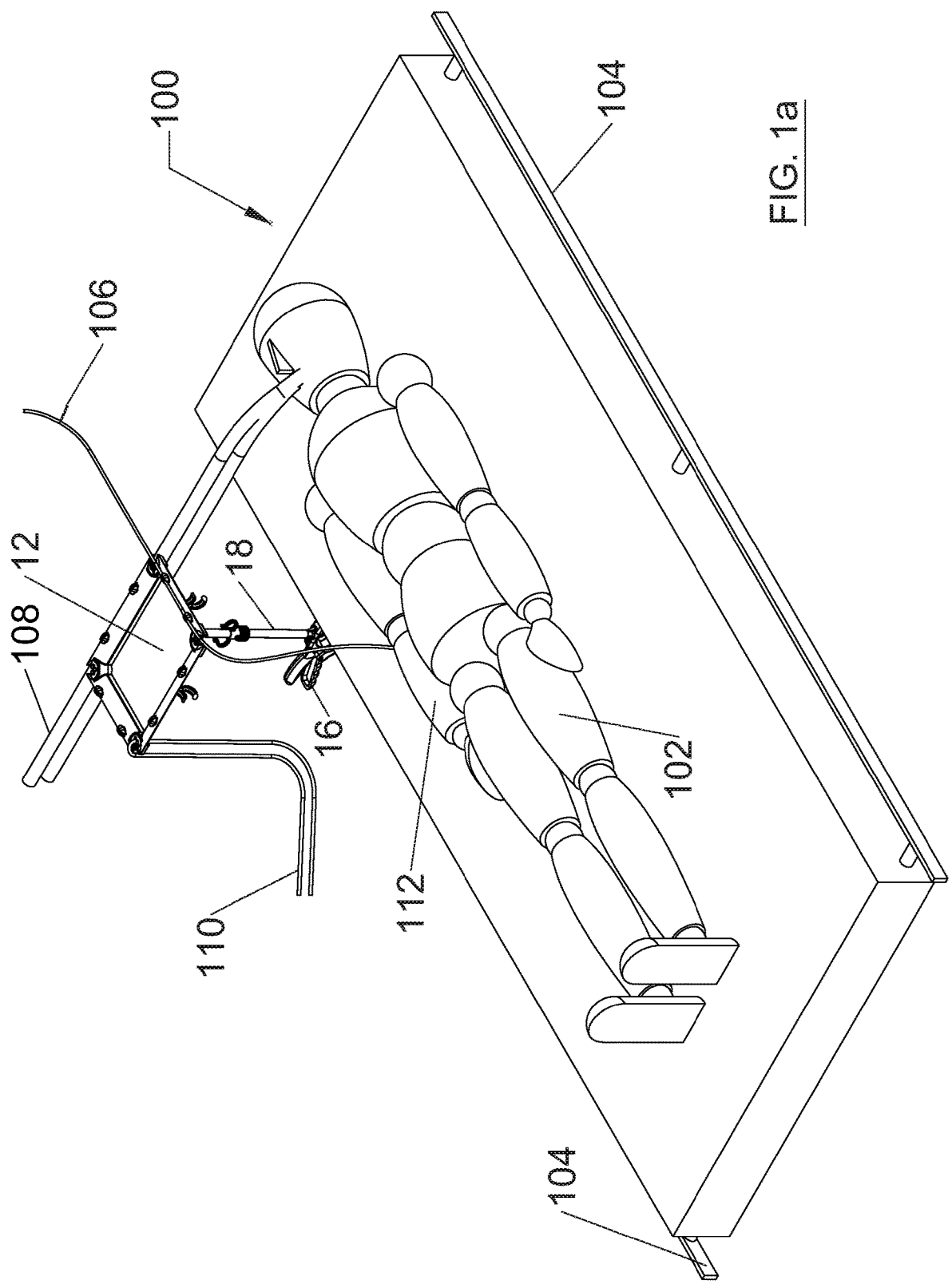
FIG. 1a is a perspective view of a medical stand configured in accordance with the present invention and secured to a side rail of an operating room bed.

Turning now to the drawings, FIG. 1a is a perspective view of a medical stand 10 configured in accordance with the present invention, wherein the medical stand 10 is secured to a railing 104 of a hospital operating bed 100. A patient 102 is shown laying on the operating bed 100, wherein a breathing tube 108 is connected to the mouth of the patient 102, and an IV tube 106 is connected to the arm 112 of the patient 102. The patient 100 is illustrated as being asleep under general anesthesia.

In accordance with the present invention, a tray 12 of the medical stand 10 is secured to the railing 104 of the operating bed 100 by a clamp 16. In further accordance with the present invention, the IV tube 106, air hose 108, and suction tubing 110 or other tubing are connected to and supported by the medical stand 10 in a safe, secure, organized, and convenient location for the anesthesiologist, and moreover, the medical stand 10 keeps the tubes and hoses off the floor where they could become tangled and unsterile.

Figure 1B:
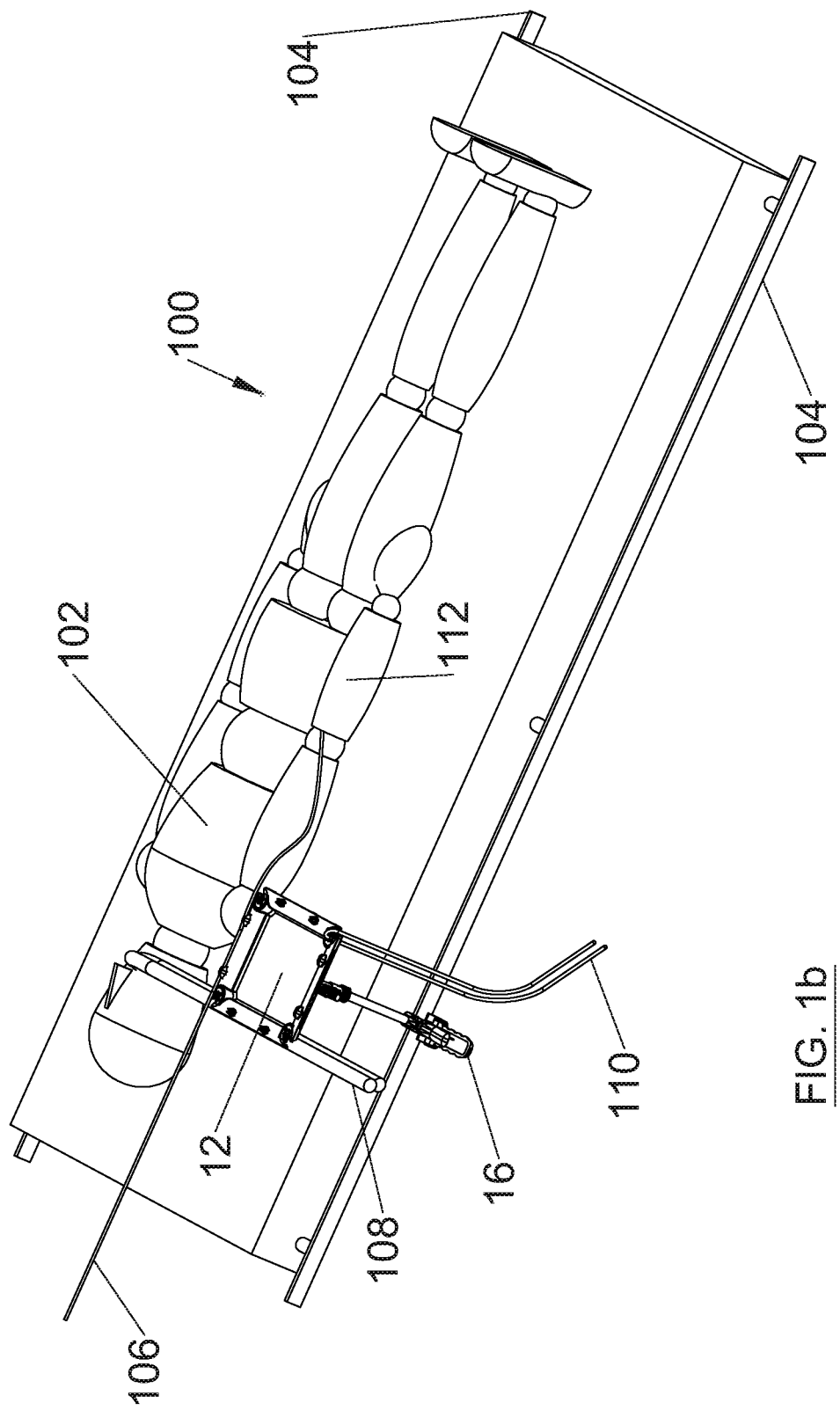
FIG. 1b is a perspective view of the medical stand shown in FIG. 1a from the opposite side of the operating room bed.

FIG. 1b is a perspective view of the medical stand 10 shown in FIG. 1 from the opposing side of the hospital operating bed 100. Shown is the clamp 16 clamped onto the bar 104 of the hospital operating bed 100. The IV tube 106, air hose 108, and suction tubing 110 or other tubing are clearly shown being connected to and supported by the medical stand 10. The IV 106 line is shown connected to the arm 112 of the patient 102, and the breathing tube 108 is shown connected to the mouth of the patient 102.

Figure 2A:
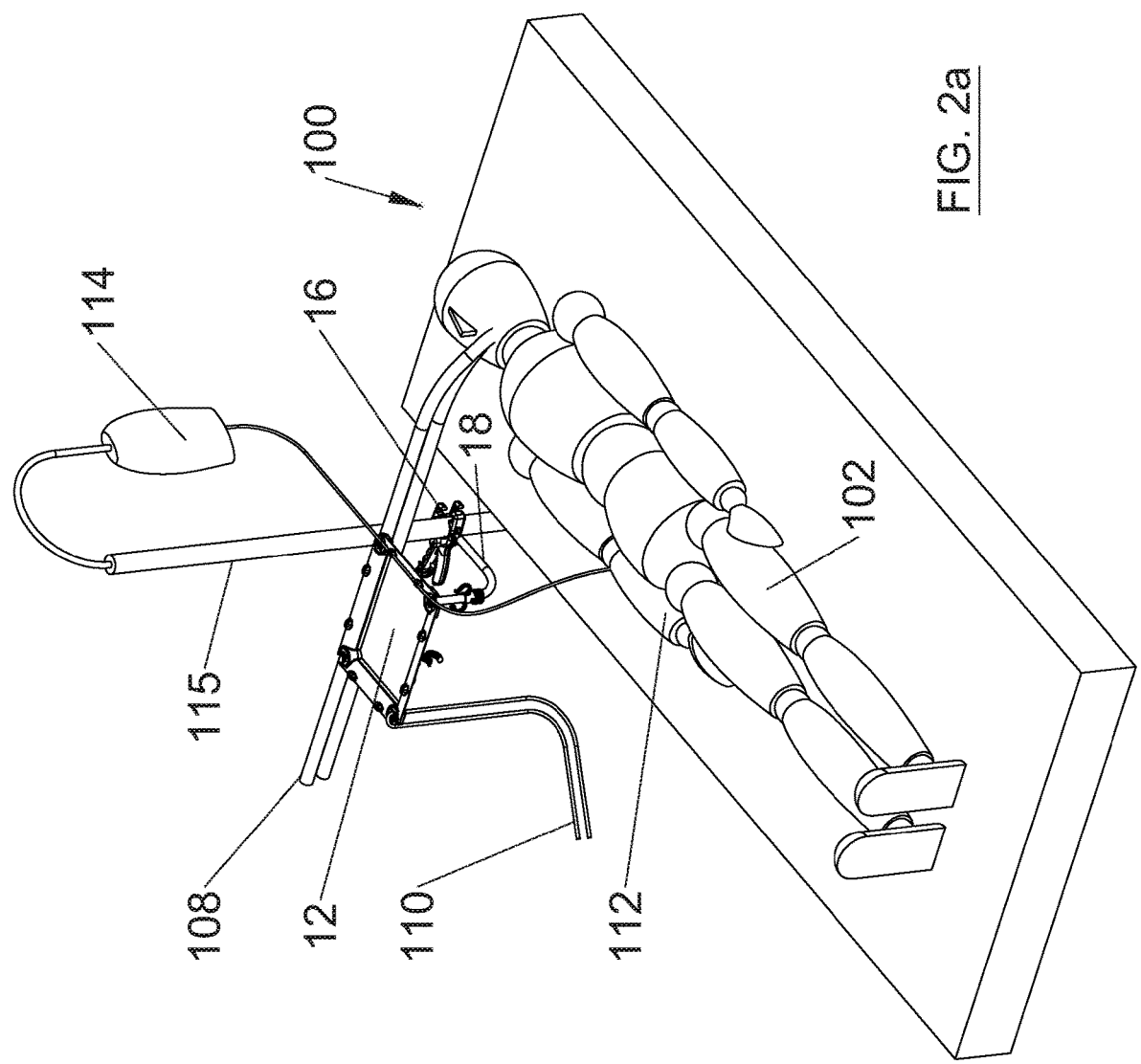
FIG. 2a is a perspective view of a medical stand shown in FIGS. 1a and 1b, except the medical stand is secured to an IV pole adjacent to the operating room bed.

FIG. 2a in perspective view of the medical stand 10 shown in FIGS. 1a and 1b, wherein the medical stand 10 is secured to an IV pole instead of the railing 104 of a hospital operating bed 100 by the clamp 16. The IV pole 115 is shown supporting an IV bag 114 connected to the IV line or tube 106. Similar to FIGS. 1a and 1b, the patent 102 is shown laying on the hospital operating bed 100, wherein the breathing tube 108 is connected to the mouth of the patient 102, and the IV tube 106 is connected to the arm 112 of the patient 102. The patient 102 is illustrated as being asleep under general anesthesia.

In accordance with another aspect of the present invention, the clamp 16 can be easily and quickly removed and secured to various fixtures, objects, or locations. This feature enables an anesthesiologists to quickly relocate and secure the medical stand 10 for convenience or to avoid interfering with a working surgeon. Regardless of the location of the medical stand 10, the medical stand 10 organizes and keeps equipment used by an anesthesiologists sterile, off the floor, at a convenient location, and out of the way of other operating equipment and the surgeon.

Figure 2B:
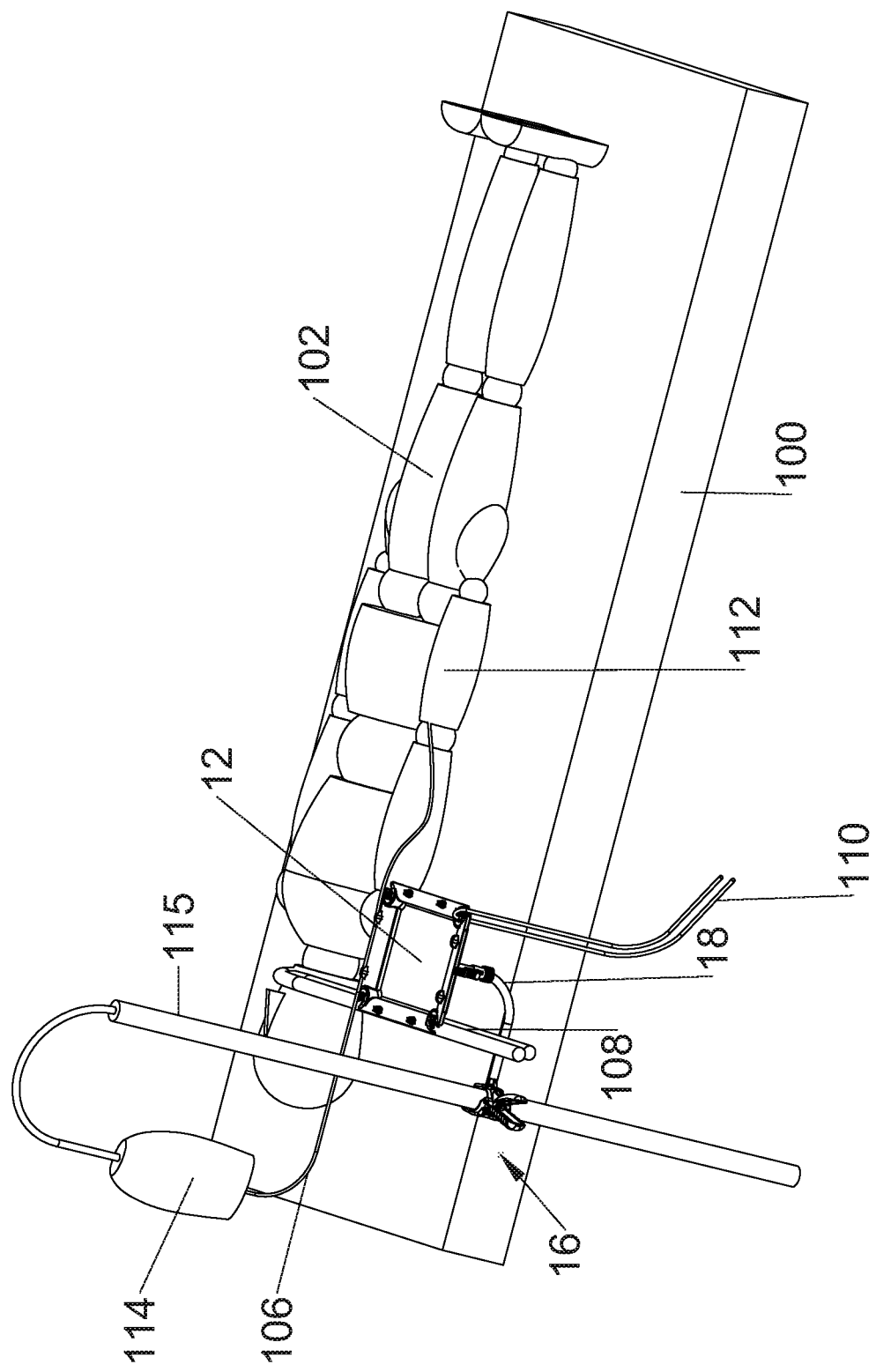
FIG. 2b is a perspective view of the medical stand shown in FIG. 2a from the opposite side of the operating room bed.

FIG. 2b is a perspective view of the medical stand 10 shown in FIG. 2a from the opposing side of the hospital operating bed 100. Shown is the clamp 16 clamped onto the IV pole 115 of the hospital operating bed 100. The IV tube 106, air hose 108, and suction tubing 110 or other tubing are clearly seen being connected to and supported by the medical stand 10. The IV line 106 is shown connected to the arm 112 of the patient 102, and the breathing tube 108 is shown connected to the mouth of the patient 102.

Figure 3A:
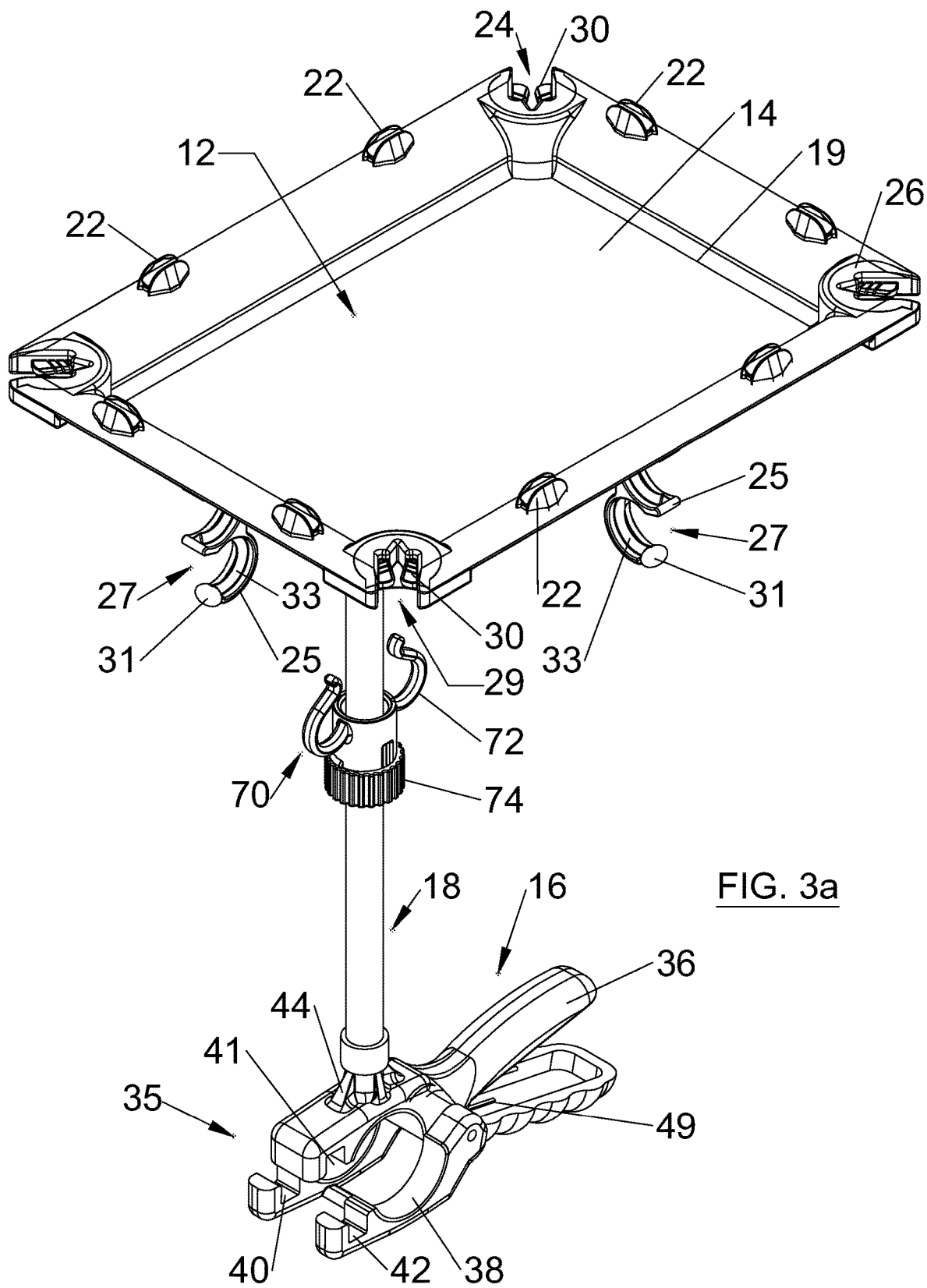
FIG. 3a is a perspective view of the medical stand shown in FIGS. 1a-2b showing a top of a tray of the medical stand.

FIG. 3a is a detailed perspective view of the medical stand 10 shown in FIGS. 1a-2b configured in accordance with the present invention. The medical stand 10 includes the tray 12 and the clamp 16. The tray 12 is connected to the clamp 16 by a flexible pole 18. The tray 12 is specifically configured for use in an operating room or an anesthetizing location. The clamp 16 is specifically designed to be quickly secured to and removed from various fixtures, objects, or locations in an operating room or any anesthetizing location.

The tray 12 includes a top surface 14 and a bottom surface 15. The perimeter 19 of the tray 10 includes an inclined or sloping rim 20 to prevent articles on the top surface 14 of the tray 12 from rolling or falling off the tray 12. The top of the rim 20 of the tray 12 includes IV clips 22 for securing IV tubing. The IV clips 22 are specifically constructed for securing IV tubing without pinching or damaging IV tubing to be located within the IV clamps 22. More specifically, the IV clamps 22 are elongated in design with rounded corners and constructed of soft, flexible material, such as a polymer, and include troughs sized to receive IV tubing. Multiple IV clamps or tubing clips 22 can be located at various locations on the rim 20 of the tray 12.

Corners 24 of the rim 20 of the tray 12 include corner inserts or inserts 26 within cutouts, openings, or slots 28 in the tray 12. The corner inserts 26 include slots 29 for receiving and securing various surgical items, such as flexible tubing. The slots 29 include flexible tabs or wings 30 for gently holding articles or within the slots 29 without crushing the articles. For example, an endotracheal tube, hand suction probe and tubing, ultrasound probe cord, or tubing for invasive monitoring can be safely held within the slots 29 by the flexible tabs 30 without crimping or collapsing flexible tubing.

Multiple breathing tube clips 25 specifically designed for holding corrugated or expandable breathing tubes or tubing 108 are connected to the tray 12, preferably on the bottom surface 13 (FIG. 3b) of the tray 12. The breathing tube clips 25 include multiple semicircle openings 27 for receiving and securing breathing tubes, or ventilator circuit tubing or anesthesia machine tubing. The breathing tube clips 25 can be located anywhere on the tray 12, but are preferably connected to the bottom 13 of the tray 12 as illustrated. The semicircle openings 27 of the breathing tube clips 25 include ridges 33 specifically designed for mating with the folds of corrugated breathing tubes. The ends of the breathing tube clips 25 include rounded knobs or rounded ends 31 to prevent damaging breathing tubes being inserted or removed from the breathing tube clips 25.

The clamp 16 is connected to the bottom of the tray 12 by a flexible pole 18. The flexible pole 18 includes a gooseneck clip 70 including multiple flexible clips 72 for gently securing wires or tubing to the flexible or bendable pole 18. The gooseneck clip 70 includes a tightening nut 74 enabling the position of the gooseneck clip 70 to be moved and secured to various locations on the vertical pole 18. The gooseneck clip 70 holds cords and wires in a way that allows them to be easily placed and removed. The gooseneck clip 70 preferably is constructed of a flexible polymer or plastic.

The clamp 16 includes specialized openings in the jaws or gripping surfaces 35 of the clamp 16 at the opposing ends of the handle 36. An enlarged image of the clamp 16 is illustrated in FIG. 4. The clamp 16 binds to a fixed support to position the tray 12 in a useful location. The clamp 16 includes handles 36 to be squeezed closed by a spring or elastic substance. Examples of fixed supports include an operating room table, a hospital bed, a railing, or an IV pole. The clamp 16 is specifically designed to be secured to various location or structures in an operating room.

The vertical pole or post 18 preferably is flexible or bendable. The stiffness and strength of the post 18 is determined by the load the pole 18 needs to bear. The length of the pole 18 is determined by the specific medical need. The pole 18 is removable from the clamp 16 and tray 12 to exchange for different poles having different characteristic for different needs, such as pliability, strength, load bearing, or specific materials. The pole 18 allows the tray 18 to rotate or be adjusted to the most helpful or desired location or position for an anesthesiologist. For example, FIGS. 2a and 2b illustrate how the flexible pole 18 can be bent for properly position the tray 12.

Figure 3B:
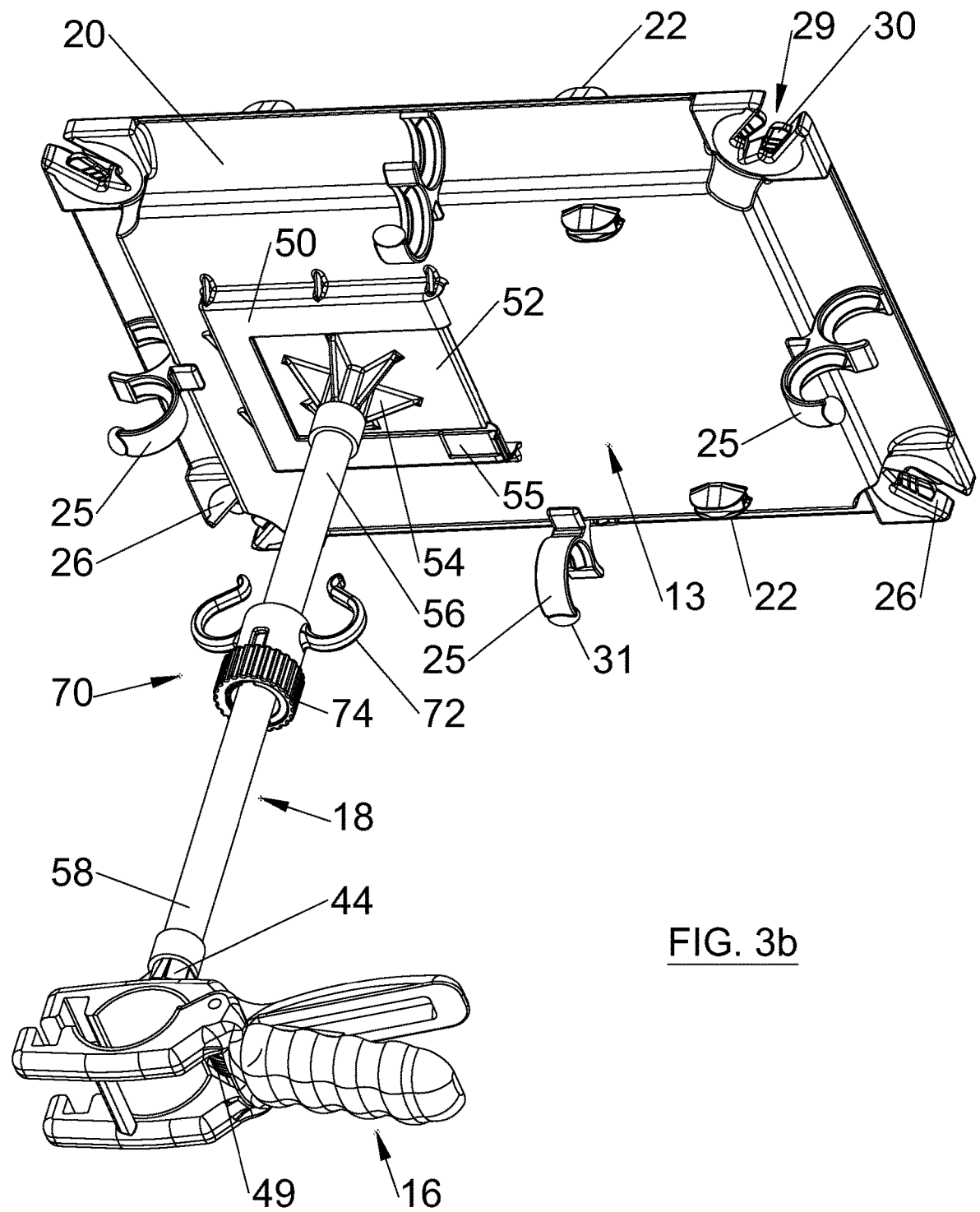
FIG. 3b is a perspective view of the medical stand shown in FIG. 3a from below the tray of the medical stand.

FIG. 3b is a perspective view of the bottom 13 of the tray 12 of the medical stand 10. Shown on the bottom 13 of the tray 12 are the breathing tube clips 25 and IV clips 22. The corner inserts 26 are shown within the slots 28 in the corners 24 of the tray 12. Slots 29 also are illustrated within the corner inserts 26. The clip or clamp 16 and the pole 18 also are illustrated.

In accordance with a further aspect of the present invention, a receptacle or slot 50 is connected to the bottom 13 of the tray 13 for slidably receiving a plate 52 to secure the pole 18 to the bottom 13 of the tray 12. A bracket 54 is connected to the top or first end 56 of the pole 18. The plate 52 is mounted to the bracket 54, and the plate 52 is mounted perpendicular to the pole 18. The plate 52 slides into the receptacle 50 to secure the tray 12 to the pole 18. The planar plate 52 provides additional support and stability to tray 12 when mounted to the pole 18. A depressible tab or releasable latch 55 is provided to secure and release the plate 52 from within the receptacle 50. The tray 12 can be released from the pole 18 without the use of a tool. The tray receptacle 50 and plate 52 removable connection mechanism enables the tray 12 to be replaced or exchanged with a different tray configuration to accommodate potential different working requirements. A bracket 44 is located on the clamp 16 for securing the second end or bottom 58 of the pole 18 to the clamp 16.

FIG. 4 illustrates and enlarged view of the clamp 16 shown in FIGS. 1a-3b. Illustrated are pivotally mounted handles 36 and the upper jaw 35 and the lower jaws 37, 39. The lower jaws 37, 39 can be referred to as double jaws, divided jaws, or splits jaws. A spring 49 is located within the handles 36 to prove a constant force to keep the jaws 152, 154 closed. The upper jaw 35 is located between the lower jaws 37, 39 thus enabling the upper jaw 35 to "pass by" or in between the lower jaws 37, 39 at the clamp is closed. Furthermore, the jaws 37, 39 rotate in different planes, thus enabling the jaws to pass by each other in the closed position. Both the upper jaw 35 and the lower jaws 37, 39 include a semicircle cutout or notch 38 for clamping onto a circular fixture or object, such as an IV pole. In order to securely clamp around poles and other circular objects of varying diameters, the upper jaw 35 is designed to "pass by" the lower jaws 37, 39 (see FIGS. 10a and 10b). This enables the clamp 16 to securely grasp poles having very small diameters.

Similarly, the upper jaw 35 includes a rectangular slot or notch 41, and the lower jaws 37, 39 include rectangular slots or notches 40,42. These slots 40, 41, 42 enable the clamp 16 to securely grasp rectangular bars or other rectangular objects or fixtures, such as the rectangular railing 104 of the hospital operating bed 100. A locking mechanism, similar to a vice grip wrench, can be included to prevent the clamp 16 from accidental slipping off a fixed support. Furthermore, a non-slip surface can be including on the gripping surface of the jaws 35, 37, 39 prevent slipping of the clamp.

A bracket 44 is attached to the upper jaw 35 for securing the second end of the pole 18 to the clamp 16. The bracket includes an aperture 45 for receiving and securing the pole 18 within the aperture 45. The aperture 45 preferably is sized for tightly securing the pole 18 within the aperture 45 by friction. The apertures 45 also can be lined with a non-slip surface to prevent the pole 18 from being easily removed from the aperture 45.

FIG. 5a is a perspective view of the top 14 of the tray 12 shown in FIGS. 1a-3b, wherein only the tray 12 is shown. In addition to the pole 18 and the clamp 16, the corner inserts 26 and the IV clips 22 have been removed. Mounting holes and posts 59 in the rim 20 of the tray 12 for the IV clips 22 can be seen.

Figure 5B:
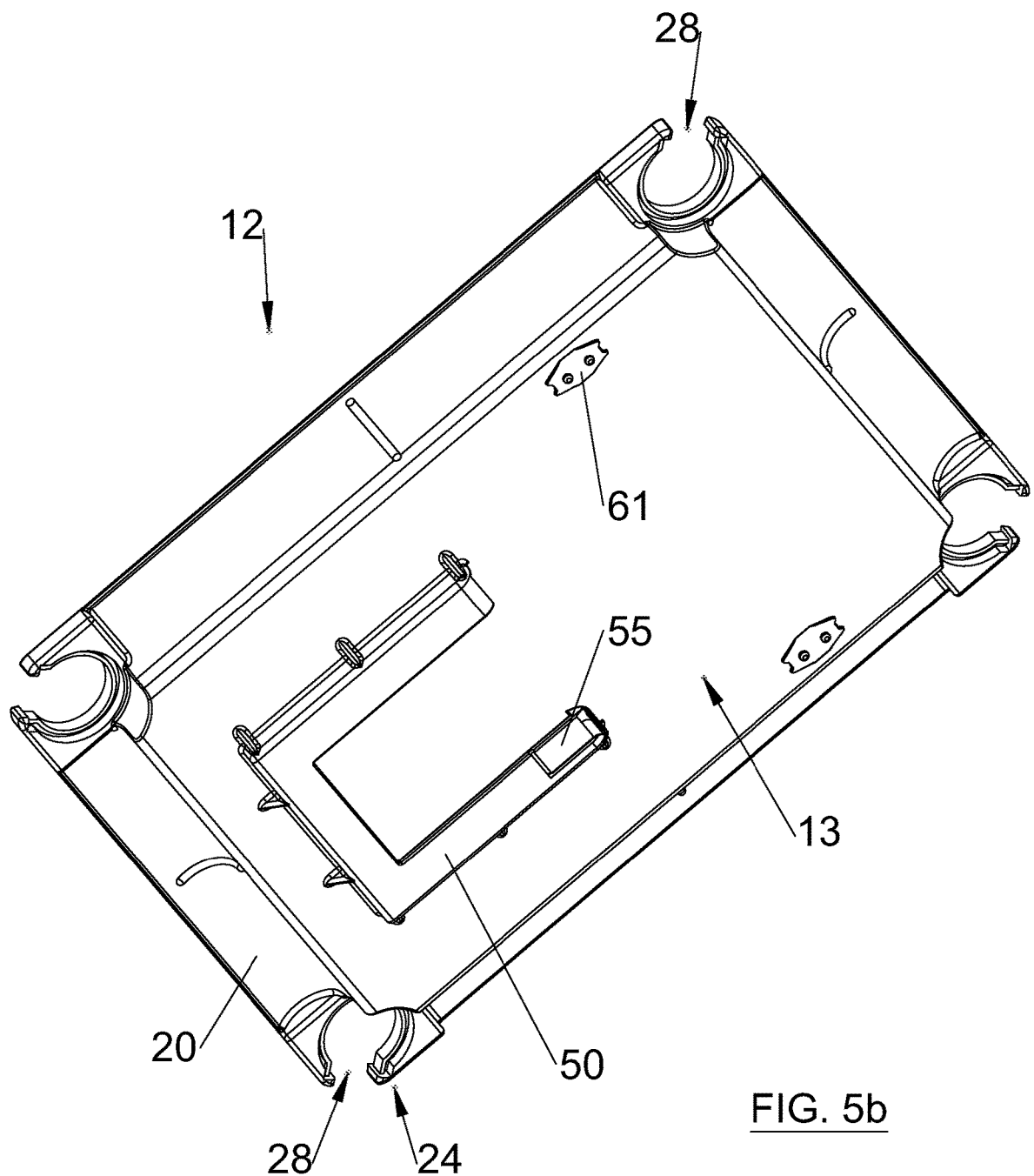

FIG. 5b is a perspective view of the bottom 13 of the tray 12 shown in FIG. 5a. Illustrated are the slots 28 in the corners 24, and the bottom of the rim 20. Mounting holes and post 61 for the IV clips 22 are shown, as well as the mounting receptacle 50 and the locking and release tab 55.

Figure 6:
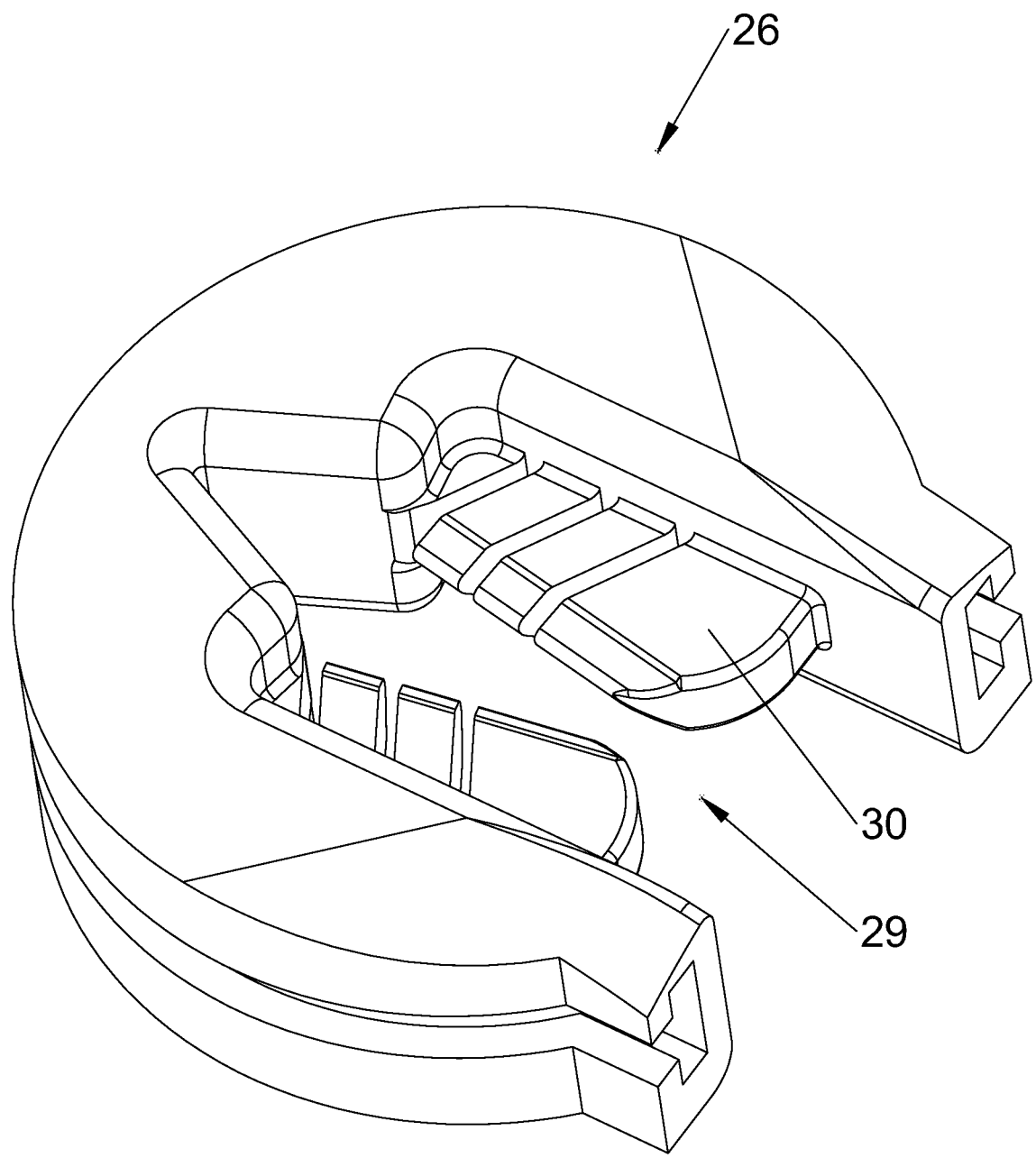
FIG. 6 is a perspective view of the corner insert shown in FIGS. 3a and 3b.

FIG. 6 is an enlarged perspective view of the corner insert 26 shown in FIGS. 3a and 3b. The corner insert 26 is preferably molded from a flexible material, such as rubber or a flexible polymer. The wings 30 within the slot 29 of the corner insert 26 are preferably molded as a single unit.

Figure 7A:
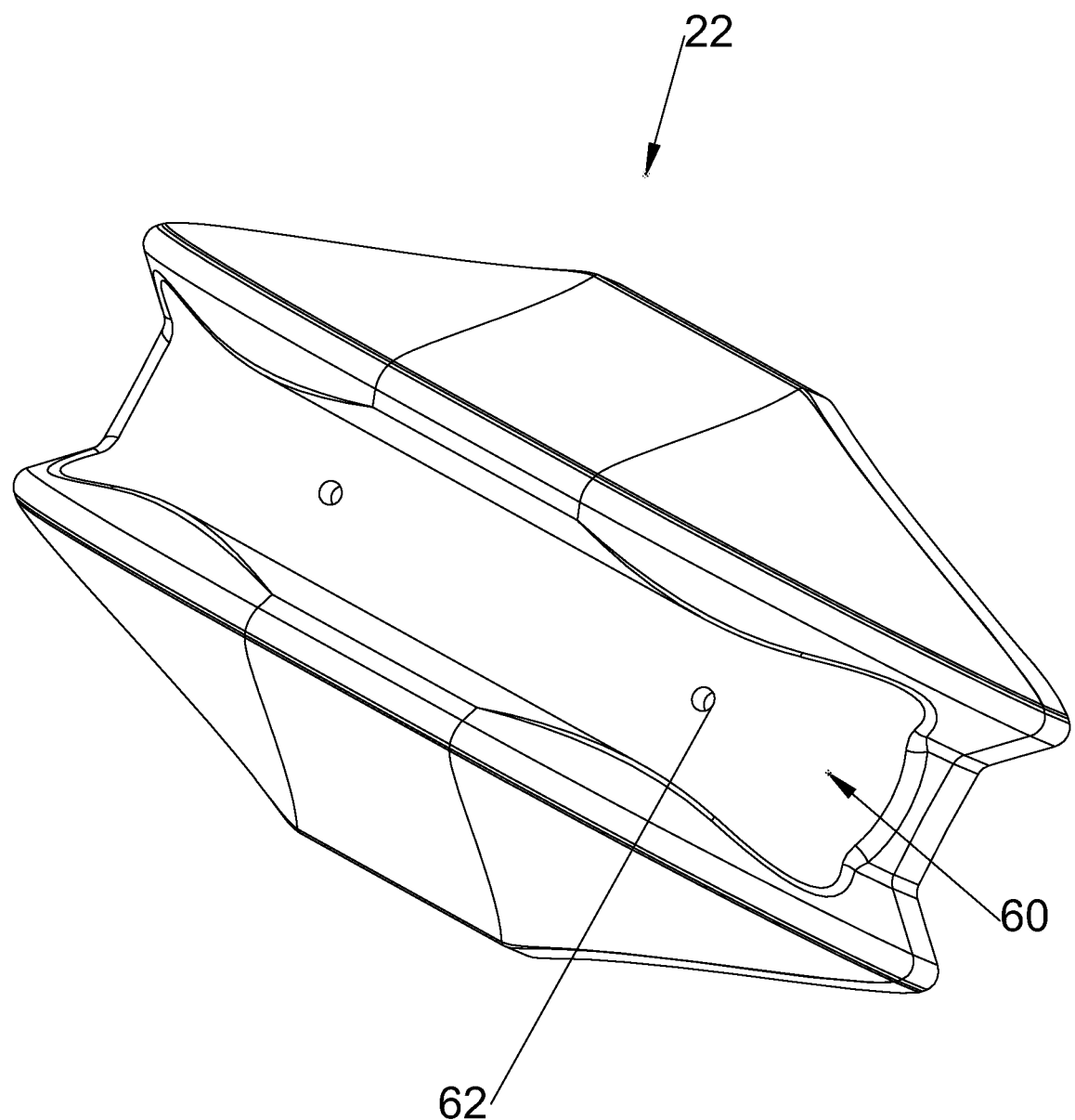
FIG. 7a is a perspective view of the top of the IV clip shown in FIGS. 3a and 3b.

FIG. 7a is perspective view of the top of the IV clip 22 shown in FIGS. 3a and 3b. Illustrated are mounting holes 62 within the bottom of the trough 60 of the IV clip 22.

Figure 7B:
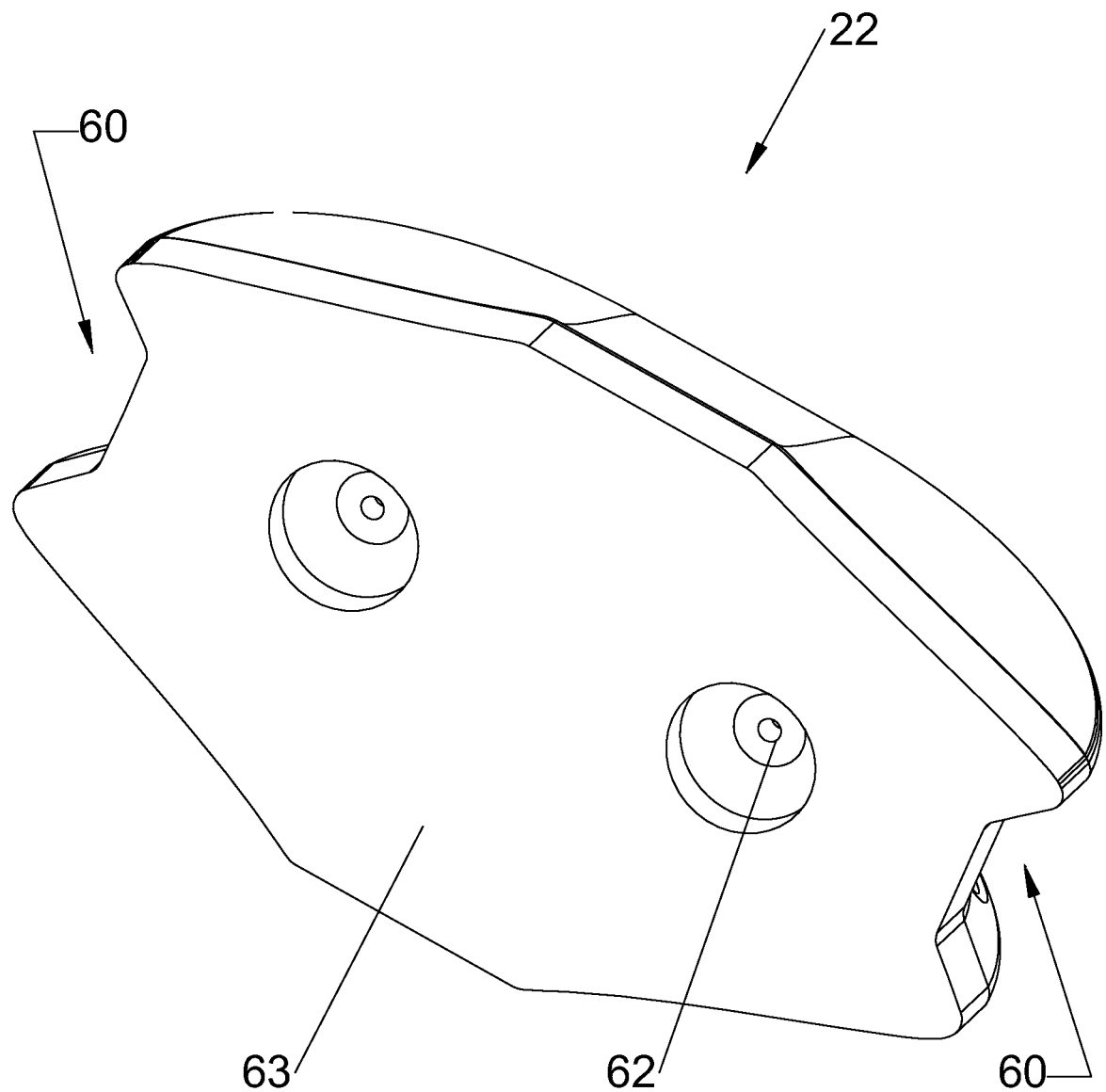
FIG. 7b is a perspective view of the bottom of the IV clip shown in FIGS. 3a and 3b.

FIG. 7b is a perspective view of the bottom 63 of the IV clip 22. The mounting apertures or holes 62 are shown and the trough 60.

Figure 7C:
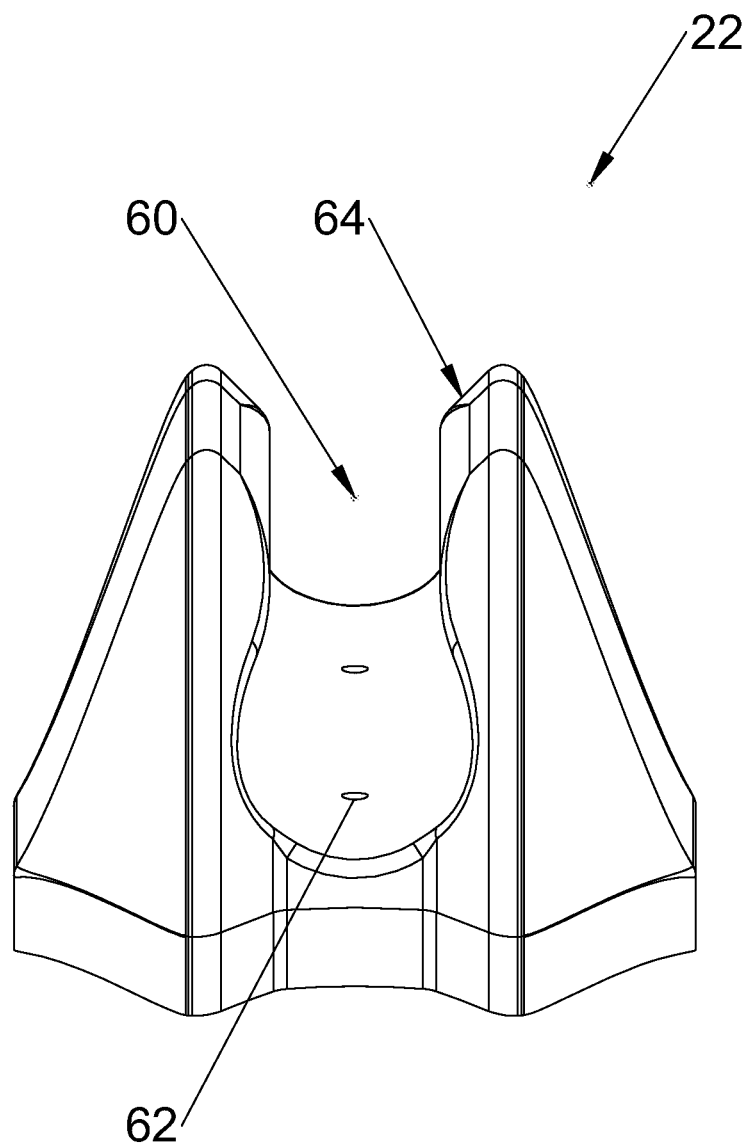
FIG. 7c is a perspective view of the end of the IV clip 22.

FIG. 7c is a perspective view of the end of the IV clip 22. Shown are the mounting holes 62 in the bottom of the trough 60 which is sized for receiving IV tubing. Also shown are the tabs or rounded upper walls 64 of the trough 60 for securing an IV tube within the flexible IV clip 22 without damaging IV tubing. The IV clips 22 preferably are constructed of a flexible material, such as rubber, to expand and gently secure IV tubing within the trough 60. The edges on all corners of the IV clip 22 are smooth and round to prevent the IV clip 22 from cutting or damaging IV tubing being placed within or removed from the trough 60.

Figure 8:
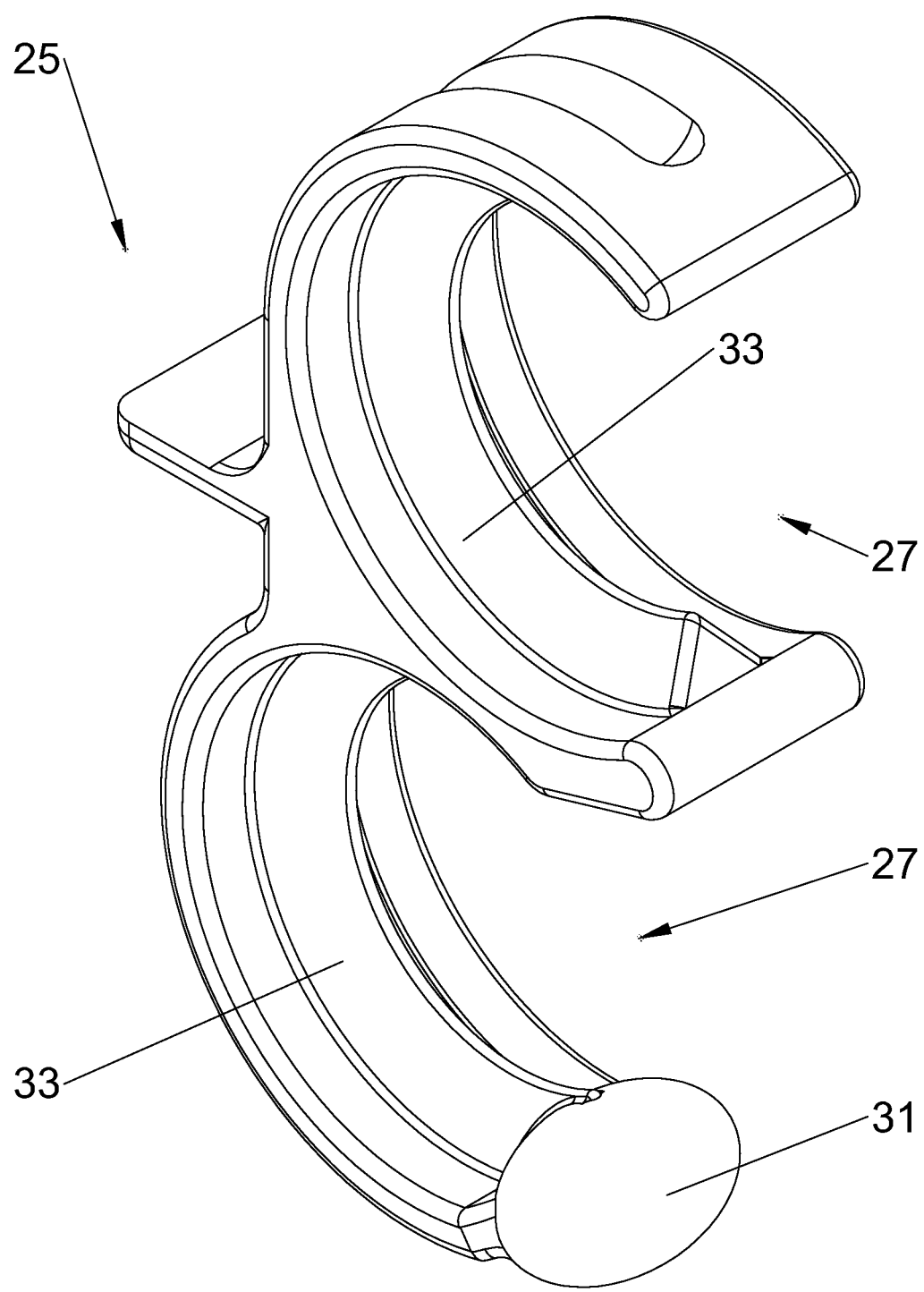
FIG. 8 is a perspective view of an air hose clip shown in FIGS. 3a and 3b.

FIG. 8 is an enlarged perspective view of the breathing tube clip 25 shown in FIGS. 3a and 3b. The semicircle openings 27 of the breathing tube clips 25 are shown including ridges 33 specifically designed for mating with the folds of corrugated breathing tubes. The ends of the breathing tube clip 25 includes rounded knobs or rounded ends 31 to prevent damaging breathing tubes being inserted or removed from the breathing tube clips 25. The breath tube clip 25 is preferably molded as a single unit from a flexible plastic.

Figure 9A:
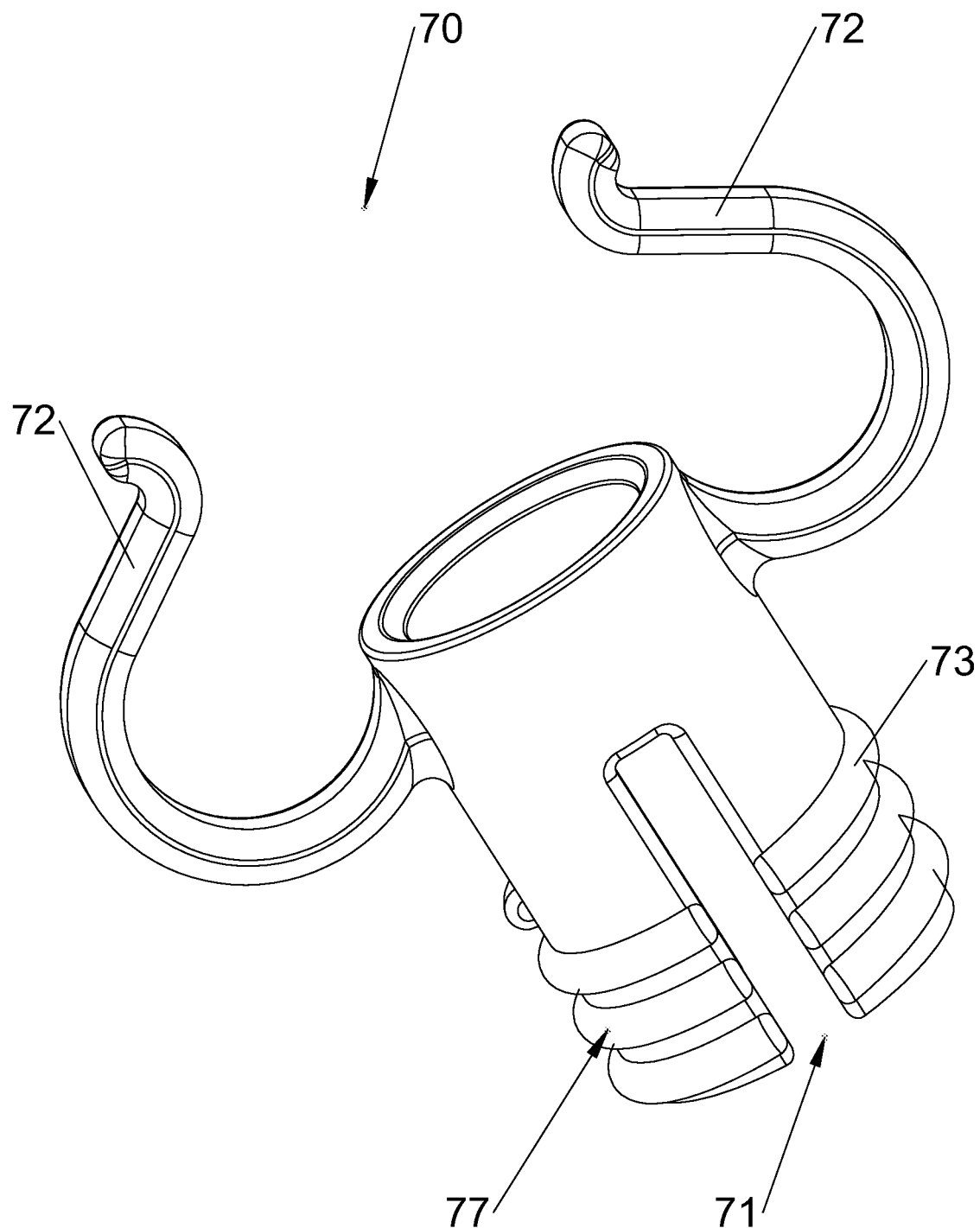
FIG. 9a is a perspective view of a pole clip configured in accordance with the present invention.

FIG. 9a illustrates the gooseneck clip 70 shown in FIGS. 3a and 3b. The Gooseneck clip 70 includes multiple flexible clips 72 for gently securing wires or tubing to the flexible or bendable pole 18. Threads 73 for a tightening nut 74 are included on the base 77 of the gooseneck clip 70, and a slot or slit 71 in the base 77 enables the diameter of the gooseneck clip 70 to be decreased to tighten the gooseneck clip 70 around the pole 18 using the tightening nut 74.

Figure 9B:
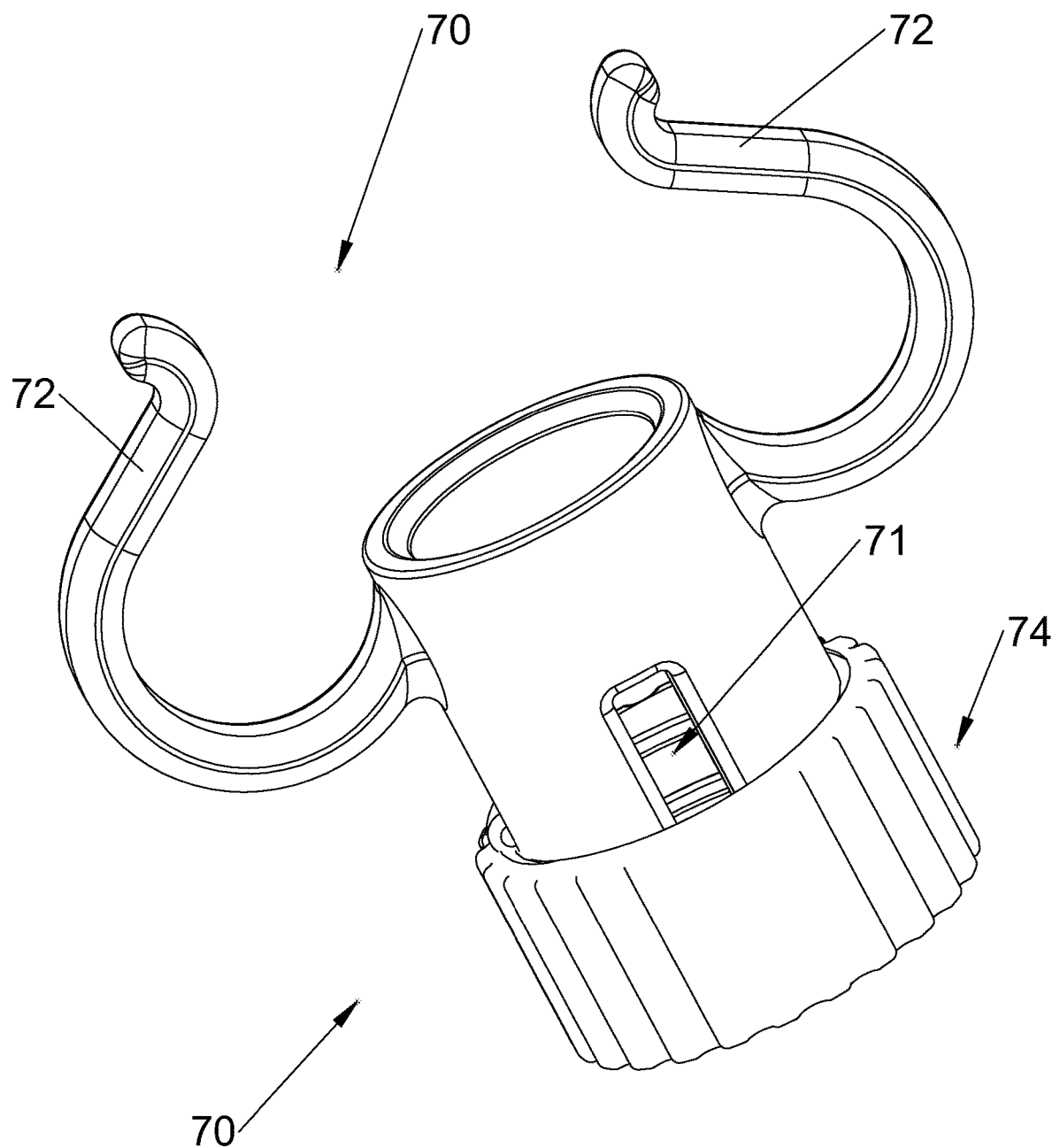
FIG. 9b is a perspective view of the pole clip shown in FIG. 9a, wherein the tightening nut also is included.

FIG. 9b shows the gooseneck clip 70 of FIG. 9a, wherein the tightening nut 74 is included around the base 77 of the gooseneck clip 70. The gooseneck clip 70 preferable is constructed out of a flexible plastic.

Figure 10A:
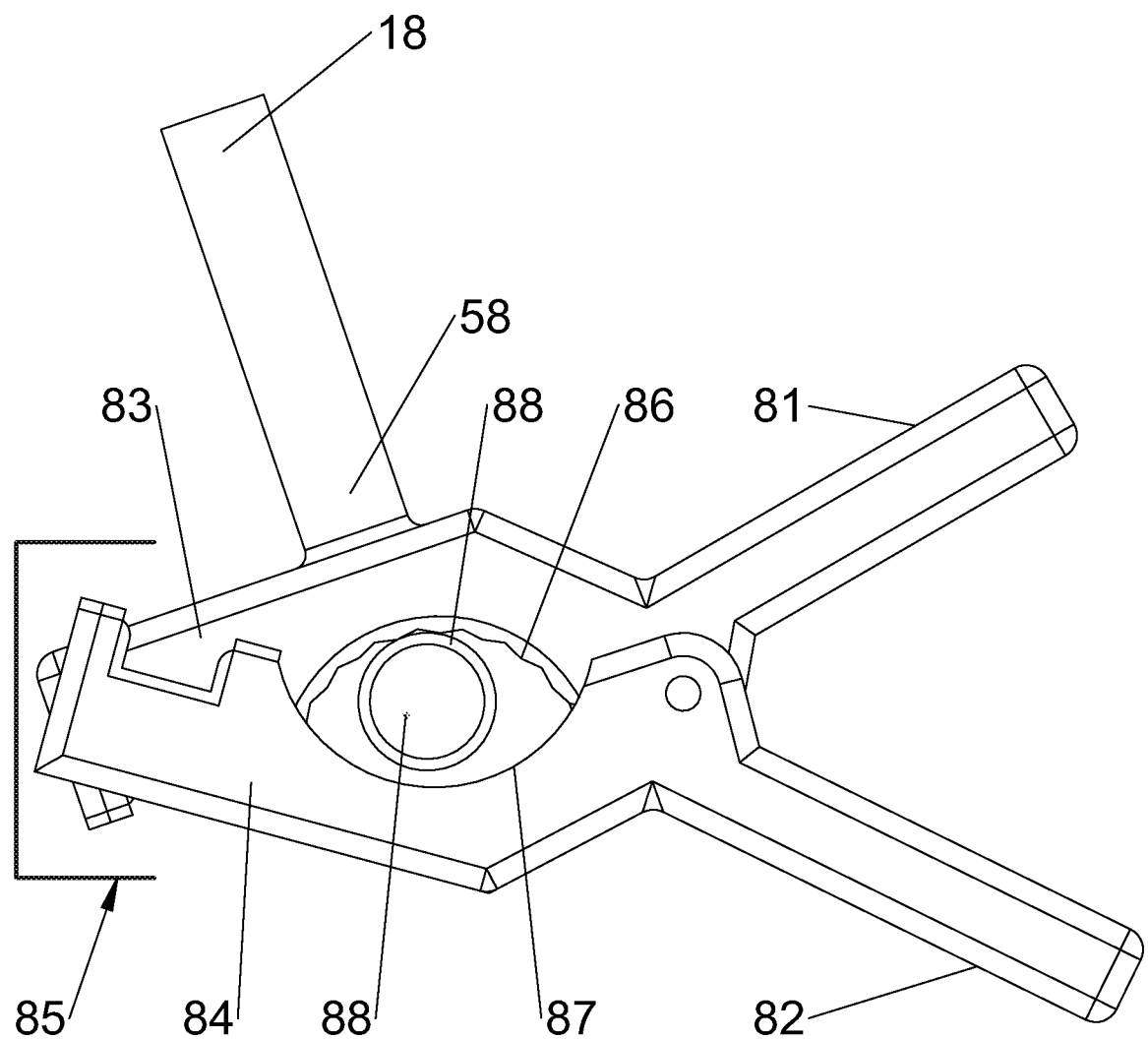
FIG. 10a is a side view of a clamp configured in accordance with another embodiment of the present invention.
Figure 10B:
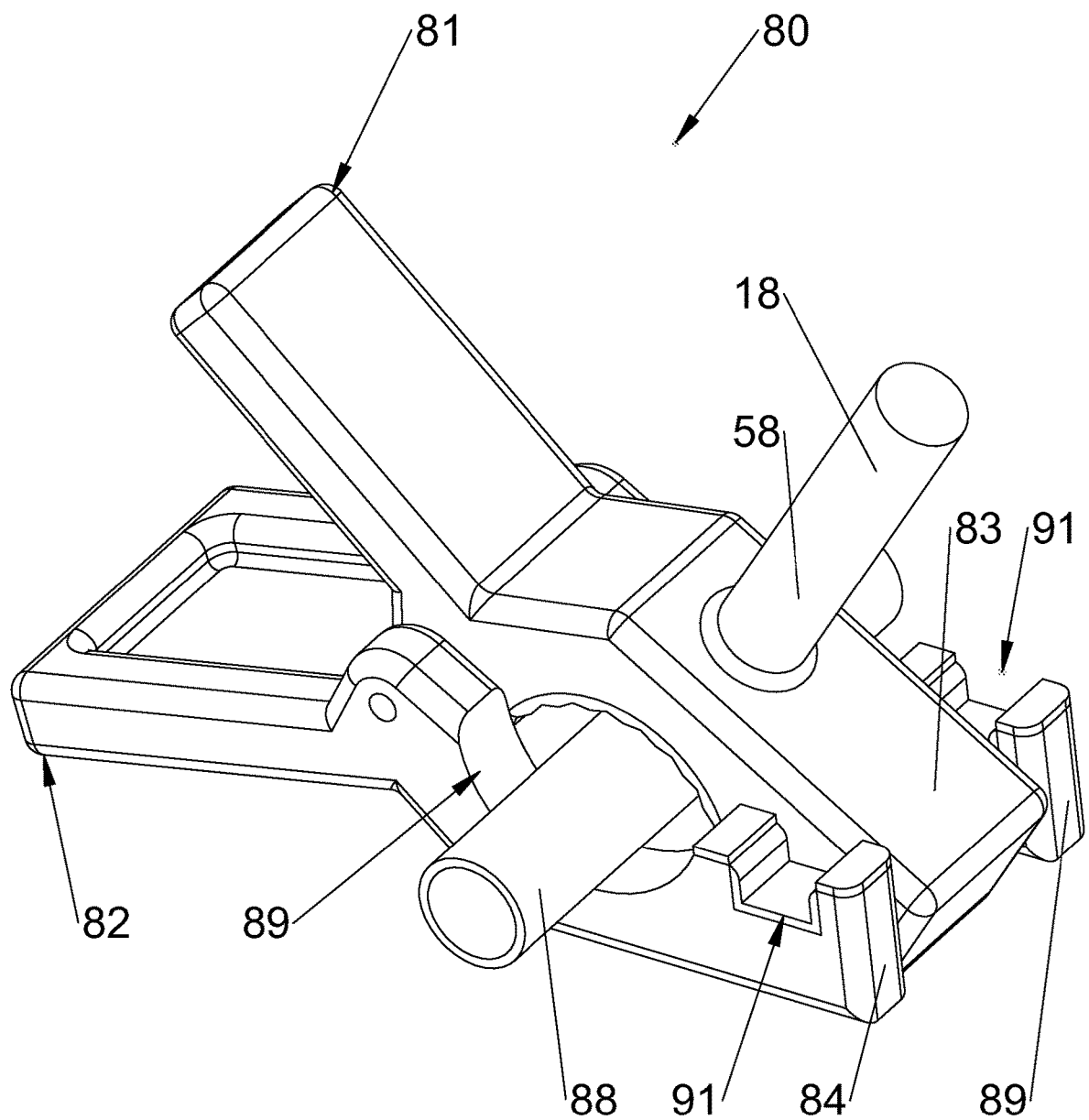

FIG. 10a is a side view of a clamp 80 configured in accordance with a second embodiment of the present invention. The clamp 80 includes handles 81, 81 and pivotally mounted jaws 83, 84 that can "pass by" each other when closed, as indicated by designated area 85. A portion of the second end 58 of the pole 18 is shown connected to the top of jaw 83. A non-slip surface 86 is included on the surface of the of the semicircle cutouts 87 in the jaws 83, 84, 89 (FIG. 10b). The clamp 80 is shown secured to a pole 88.

FIG. 10b is a perspective view of the clamp 80 shown in FIG. 10a. The "pass by" jaws 83, 84, 89 are shown in the pass by position as indicated by designation 85. Rectangular cutouts 91, 92 are shown in the lower jaws 84, 80, respectively.

Figure 11A:
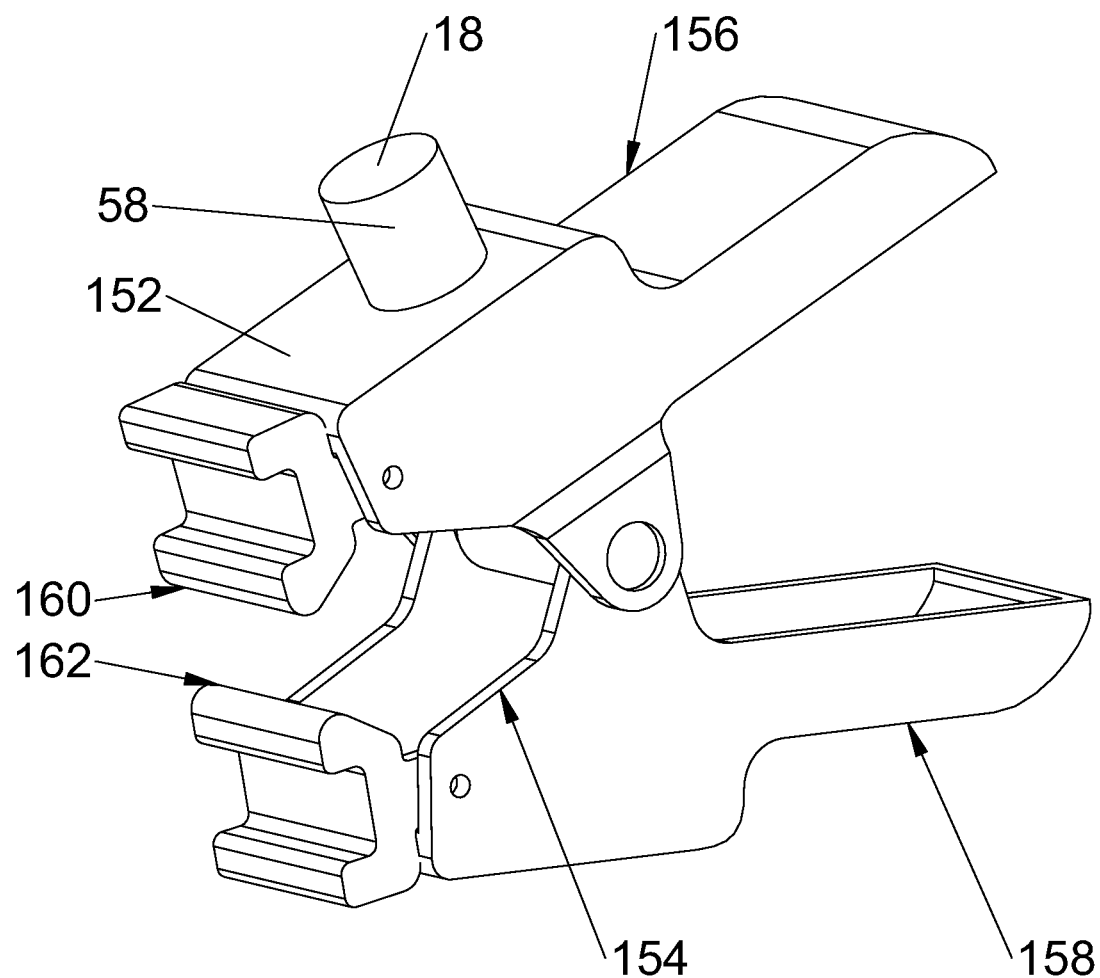
FIG. 11a is a perspective view a clamp configured in accordance with a further embodiment of the present invention.

FIG. 11a is a perspective view of a clamp 150 configured in accordance with a further embodiment of the present invention. The clamp 150 includes handles 156, 158 and pivotally mounted jaws 152, 154. The jaws 152, 154 include rotatably mounted U-bars 160, 162 that can grip various shaped objects or fixtures. A portion of the bottom or second end 58 of the flexible pole 18 is shown attached to the top of the jaw 152. Similar to clamp 16, the clamp 150 includes a spring proving a constant force to keep the jaws 152, 154 closed.

Figure 11B:
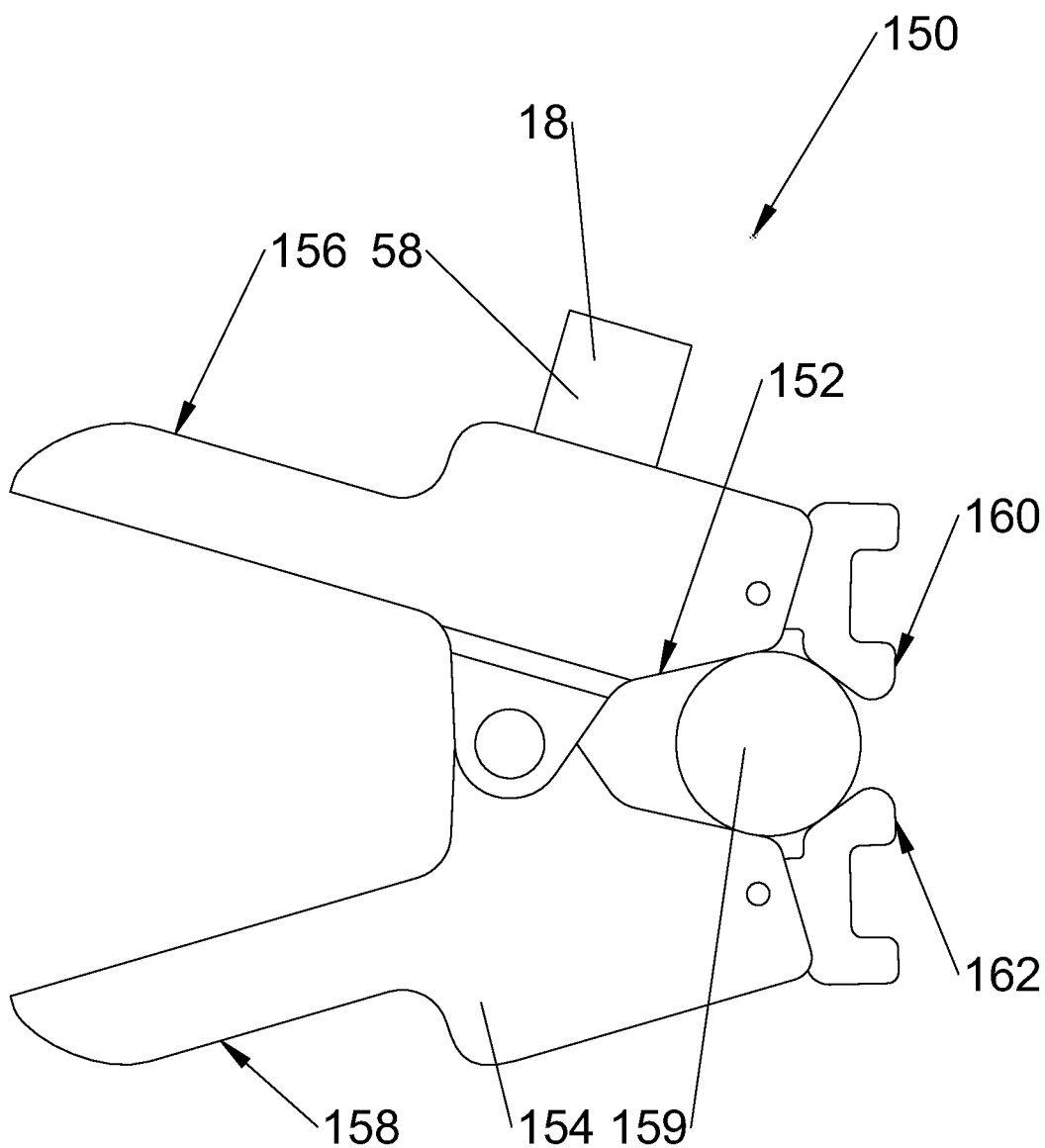
FIG. 11b is a side view of the clamp shown in FIG. 11a, wherein the clamp is secured around a small pole.

FIG. 11b is a side view of the clamp 150 shown in FIG. 11a, wherein the U-bars 160, 162 of the jaws 152, 154 are clamped around a pole 159.

Figure 11C:
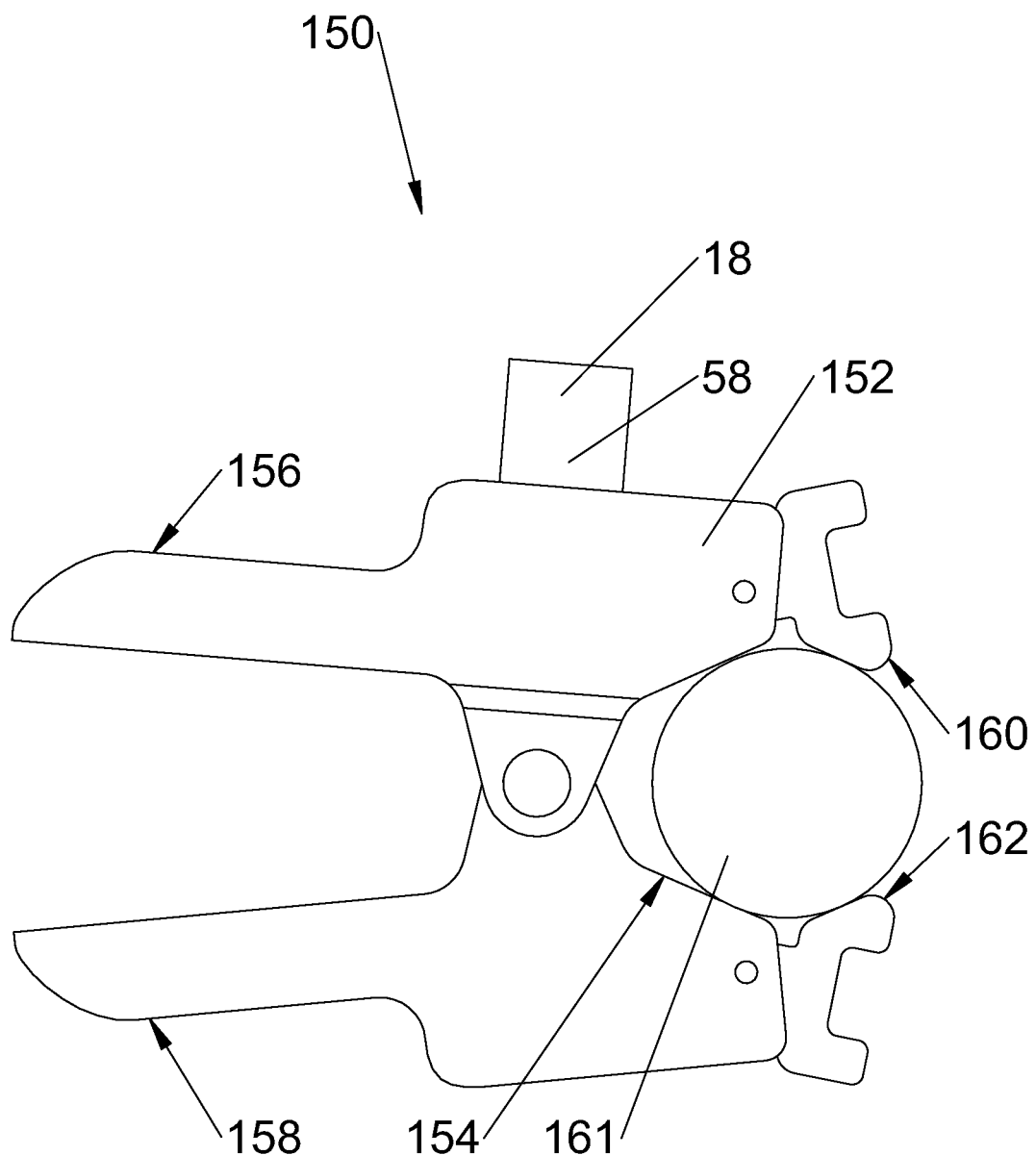
FIG. 11c is a side view of the clamp shown in FIG. 11a, wherein the clamp is secured around a large pole.

FIG. 11c is a side view of the clamp 150 shown in FIGS. 11a and 11b, wherein the U-bars 160, 162 of the jaws 152, 154 are clamped onto a larger diameter pole 161.

Figure 11D:
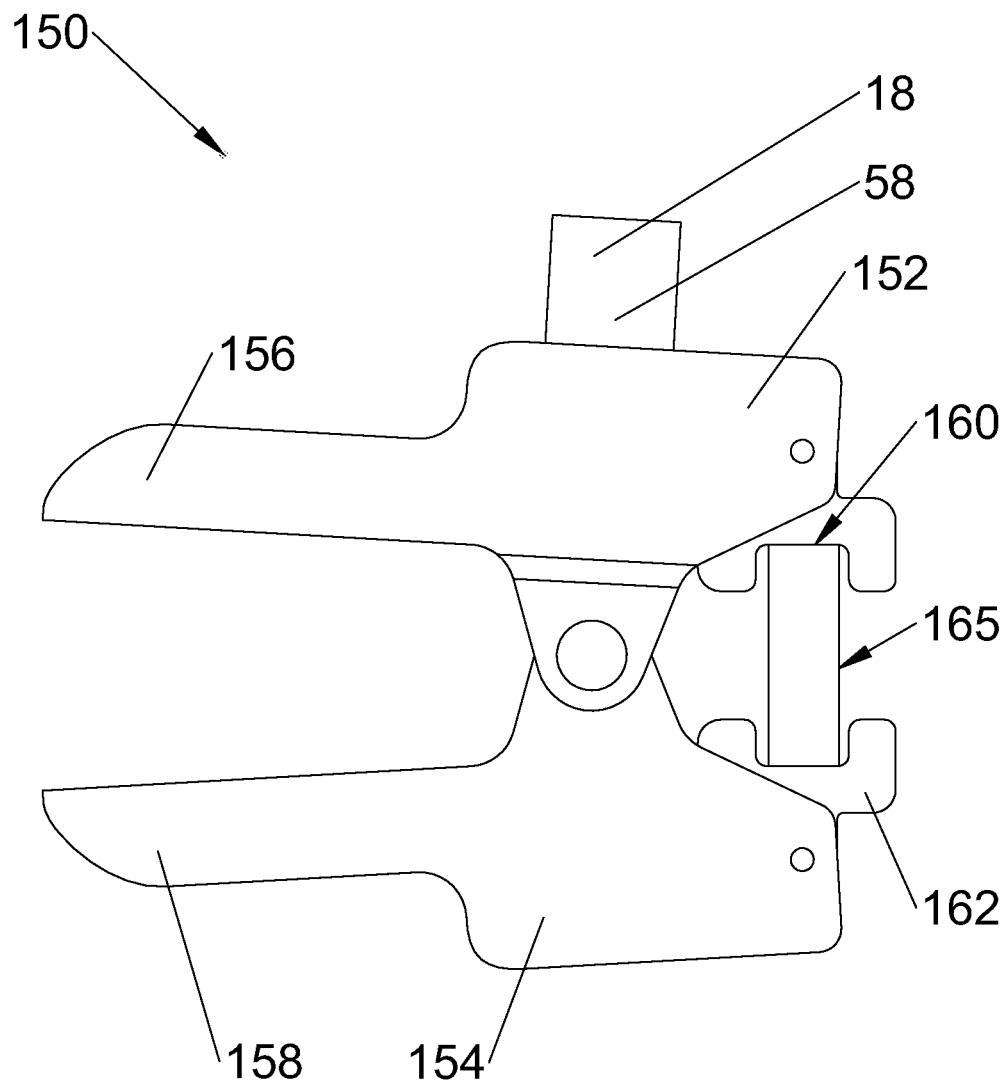
FIG. 11d is a side view of the clamp shown in FIG. 11a, wherein the clamp is secured around a rectangular bar or railing.

FIG. 11d is a side view of the clamp 150 shown in FIGS. 11a-11c, wherein the U-bars 160, 162 of the jaws 152, 154 are clamped onto a rectangular bar 165, such as the bar 104 of an operating table 100.

Figure 12:
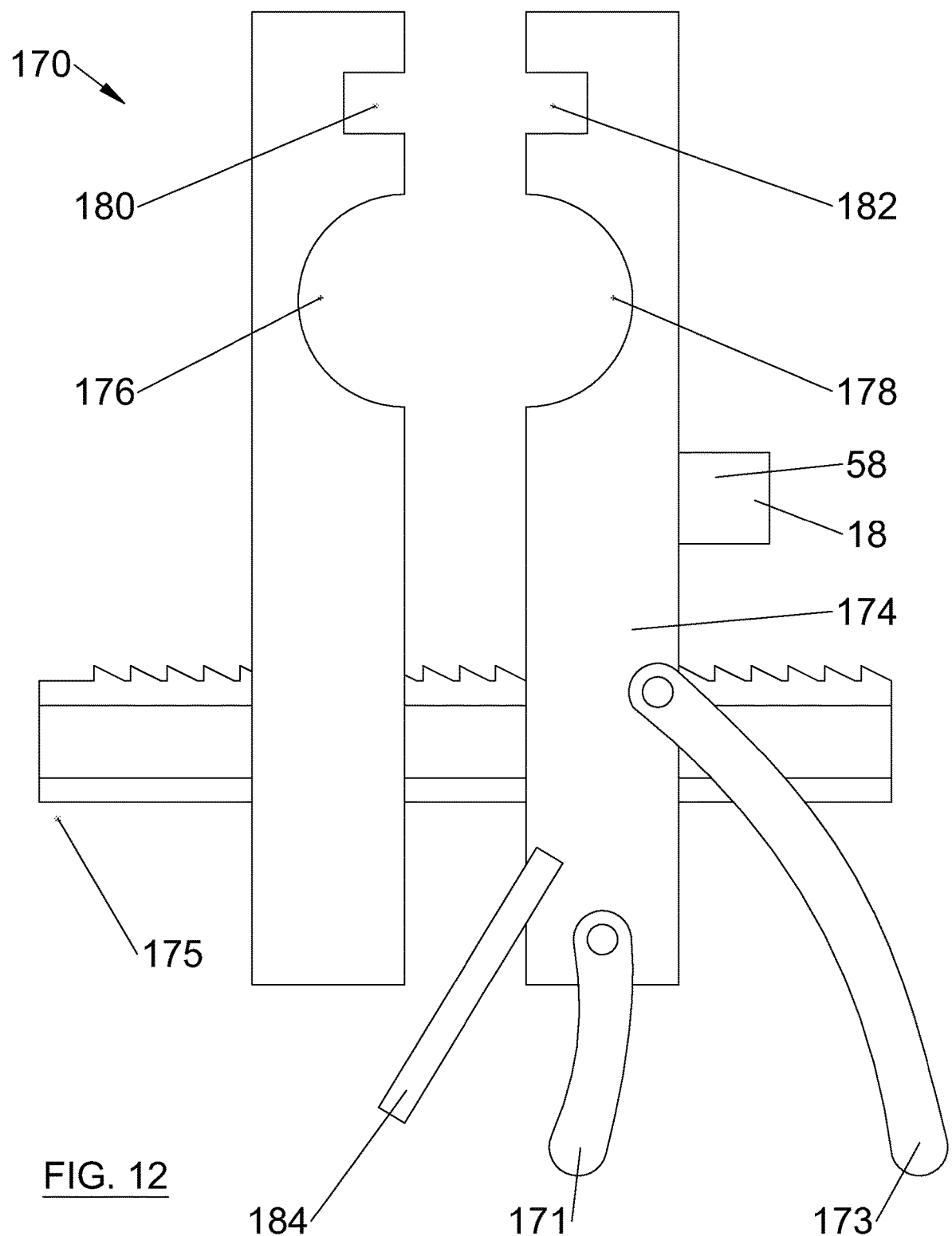
FIG. 12 is a side view of a ratchet bar clamp configured in accordance with the present invention.

FIG. 12 illustrates ratchet bar clamp 170 configured in accordance with a further embodiment of the present invention. The ratchet bar clamp 170 includes arms 172, 174 slidably attached to a toothed bar 175. The arms 172, 174 include semicircle notches 176, 178 and rectangular notches 180, 182 for securing the ratchet bar clamp 170 to various objects. Handles 171, 173 are connected to a toothed gear within the arm 174 which brings the arms 172, 174 together by squeezing handles 171, 173. The ratchet bar clamp 170 can be quickly released and removed from an object by squeezing the release trigger 184.

The invention claimed is:

1. A medical stand for use during anesthesia procedures, comprising:
   a tray having a top surface, a bottom surface, a sloping rim, and cutouts in the rim of the tray;
   a clamp to be connected to a fixed support, wherein upper and lower jaws of the clamp include circular and rectangular slots for grasping and securing the clamp to various types of stationary objects, and wherein the upper and lower jaws rotate in different planes, thus enabling the upper and lower jaws to pass by each other in a fully closed position;
   a flexible pole having a first end connected to a releasable connector on the bottom of the tray and a second end opposing the first end connected to the clamp; and
   flexible inserts located within the cutouts in the perimeter of the tray, wherein each of the flexible inserts include a flexible slot for receiving and gently securing a flexible tube.

2. The medical stand of claim 1, further comprising:
   a bed having a railing, and the clamp is secured to the railing of the bed.

3. The medical stand of claim 1, further comprising:
   an intravenous catheter (IV) pole, and the clamp is secured to the intravenous catheter (IV) pole.

4. The medical stand of claim 1, further comprising:
   an IV clip connected to the rim of the tray, wherein the IV clip is sized to receive IV tubing within a trough located on an upper surface of the IV clip.

5. The medical stand of claim 4, further comprising:
   an intravenous catheter (IV) tubing connected to the IV clip.

6. The medical stand of claim 1, further comprising:
   an air tube clip sized for receiving an air tube connected to the tray.

7. The medical stand of claim 6, further comprising:
   an air tube connected to the air tube clip.

8. The medical stand of claim 1, further comprising:
   a flexible tube located within the slot of the flexible insert.

9. The medical stand of claim 1, wherein the flexible inserts are located within corners of the tray.

10. The medical stand of claim 1, wherein the releasable connector includes a slot receptacle on the bottom surface of the tray;
    a plate sized to fit into the slot receptacle, said plate being connected to a first end of the flexible pole, and a second end of the flexible pole being connected to the clamp; and
    wherein the plate slides into the slot receptacle, thereby securing the first end of the flexible pole to the bottom surface of the tray.

11. The medical stand of claim 10, wherein the releasable connector includes a release tab connected to the slot receptacle for securing and releasing the plate from the slot receptacle.

12. The medical stand of claim 1, said clamp further comprising:
    a flexible pole receptacle on the upper jaw of the jaws of the clamp for securing the second end of the flexible pole to the upper jaw of the clamp, and the second end of the flexible pole is located within the flexible pole receptacle.

13. The medical stand of claim 1, wherein handles are connected to opposing ends of the upper and lower jaws, and the handles are rotationally mounted, and a spring is located within the handles to provide a constant force to move the upper and lower jaws to a closed position.

14. A clamp for use during anesthesia procedures, comprising:
    a clamp to be connected to an IV pole for hanging an IV bag and an IV catheter, wherein upper and lower jaws of the clamp include circular notches for grasping and securing the clamp to an IV pole, and wherein the upper and lower jaws rotate in different planes, thus enabling the jaws to pass by each other in a fully closed position and grasp IV poles; and
    said upper and lower jaws each include a rectangular notch for gripping onto a rectangular bar of a hospital bed.

15. The clamp of claim 14, further comprising:
    a tray having a top surface and a bottom surface; and a pole having a first end connected to the bottom surface of the tray and a handle of the clamp.

16. A medical stand for use during anesthesia procedures, comprising:
    a tray having a top surface and a bottom surface;
    a clamp having upper and lower jaws, wherein the upper and lower jaws each include a rectangular notch formed by three linear sides for grasping a rectangular bar;
    a pole having a first end connected to the bottom surface of the tray and a second end opposing the first end connected to the clamp; and
    wherein the upper and lower jaws are rotationally connected together and rotate in different planes, thus enabling the upper and lower jaws pass each other in a fully closed position.

17. A medical stand, comprising:
    a tray having a top surface and a bottom surface;
    a clamp having upper and lower jaws, wherein the upper and lower jaws each include a rectangular notch formed by three linear sides for grasping a rectangular bar;
    a pole having a first end connected to the bottom surface of the tray and a second end opposing the first end connected to the clamp; and
    a rotationally mounted U-bar on each of the upper and lower jaws, and the rectangular notch on each of the upper and lower jaws is located within each of the U-bars.

18. The medical stand of claim 17, wherein the upper and lower jaws are rotationally mounted together and rotate within the same plane.

* * * * *